US012702589B2

(12) United States Patent
Waid et al.

(10) Patent No.: US 12,702,589 B2
(45) Date of Patent: Aug. 11, 2026

(54) METHOD AND SYSTEM FOR CATARACT TISSUE SENSING

(71) Applicant: Johnson & Johnson Surgical Vision, Inc., Irvine, CA (US)

(72) Inventors: Christopher Waid, Cincinnati, OH (US); Cameron Nott, Fairfield, OH (US); Katrina Lieu, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 314 days.

(21) Appl. No.: 18/349,047

(22) Filed: Jul. 7, 2023

(65) Prior Publication Data

US 2025/0009556 A1 Jan. 9, 2025

(51) Int. Cl.

| | |
|---|---|
| ***A61F 9/007*** | (2006.01) |
| *A61B 17/00* | (2006.01) |
| *A61B 90/00* | (2016.01) |

(52) U.S. Cl.

CPC .. *A61F 9/00745* (2013.01); *A61B 2017/0003* (2013.01); *A61B 2017/00106* (2013.01); *A61B 2017/00199* (2013.01); *A61B 2090/064* (2016.02); *A61B 2217/005* (2013.01)

(58) Field of Classification Search

CPC ....... A61F 9/00745; A61B 2017/00199; A61B 2017/0003; A61B 2017/00106

See application file for complete search history.

(56) References Cited

U.S. PATENT DOCUMENTS

| | | | |
|---|---|---|---|
| 4,826,482 A | 5/1989 | Kamen | |
| 4,954,960 A | 9/1990 | Lo et al. | |
| 5,157,603 A | 10/1992 | Scheller et al. | |
| 5,160,317 A | 11/1992 | Costin | |
| 5,279,547 A * | 1/1994 | Costin ................ | A61F 9/00745 604/22 |

(Continued)

FOREIGN PATENT DOCUMENTS

| | | |
|---|---|---|
| DE | 3234621 A1 | 3/1984 |
| EP | 0741554 A1 | 11/1996 |

(Continued)

OTHER PUBLICATIONS

U.S. Appl. No. 16/727,100, titled "Phacoemulsification Apparatus," filed Dec. 26, 2019.

(Continued)

*Primary Examiner* — Mong-Shune Chung

(57) ABSTRACT

Systems and methods for sensing tissue in a phacoemulsification procedure are provided herein. A method may include generating a sensing signal through a frequency range centered at a local resonant frequency of an ultrasonic handpiece and measuring impedance characteristics of the signal at a distal end of a needle of an ultrasonic handpiece. A method may further include comparing the measured impedance characteristics of the generated sensing signal with one or more stored impedance profiles. A method may further include classifying, based on the comparison between the measured impedance characteristics and the stored one or more impedance profiles, a medium contacting the distal end of the needle. A method may further include controlling an output of the ultrasonic handpiece based on the classification of the medium contacting the tip of the needle.

20 Claims, 26 Drawing Sheets

(56) References Cited

U.S. PATENT DOCUMENTS 5,733,256 A 3/1998 Costin
5,836,990 A 11/1998 Li
6,690,280 B2 2/2004 Citrenbaum et al.
7,727,193 B2 6/2010 Boukhny et al.
7,842,005 B2 11/2010 Kadziauskas et al.
8,048,020 B2 11/2011 Boukhny et al.
8,246,580 B2 8/2012 Hopkins et al.
8,414,605 B2 4/2013 Gordon et al.
8,523,812 B2 9/2013 Boukhny et al.
8,597,228 B2 12/2013 Pyles et al.
9,144,517 B2 9/2015 Kuebler et al.
9,282,989 B2 3/2016 Boukhny et al.
9,522,221 B2 12/2016 Muri et al.
9,545,335 B2 1/2017 Boukhny et al.
9,707,127 B2 7/2017 Kadziauskas et al.
9,999,710 B2 6/2018 Ross et al.
10,045,882 B2 8/2018 Balicki et al.
10,070,988 B2 9/2018 Mcdonell et al.
10,219,940 B2 3/2019 Raney et al.
10,368,760 B2 8/2019 Hauck
10,453,571 B2 10/2019 Teodorescu
10,463,780 B2 11/2019 Mallough et al.
10,596,033 B2 3/2020 Urich et al.
10,940,039 B2 3/2021 Banko
11,141,313 B2 10/2021 Zhang et al.
11,317,937 B2 5/2022 Nott et al.
11,399,858 B2 8/2022 Sawhney et al.
11,464,559 B2 10/2022 Nott et al.
11,612,408 B2 3/2023 Yates et al.
12,127,979 B2 10/2024 Gliner et al.
2004/0092800 A1 5/2004 Mackool
2004/0193182 A1 9/2004 Yaguchi et al.
2005/0209560 A1 9/2005 Boukhny et al.
2005/0261628 A1 11/2005 Boukhny et al.
2006/0079788 A1 4/2006 Anderson et al.
2006/0100570 A1 5/2006 Urich et al.
2006/0129140 A1 6/2006 Todd et al.
2006/0224107 A1 10/2006 Claus et al.
2007/0073309 A1 3/2007 Kadziauskas et al.
2007/0161972 A1 7/2007 Felberg et al.
2008/0064935 A1 3/2008 Wong et al.
2008/0147023 A1 6/2008 Hopkins et al.
2009/0118663 A1 5/2009 Rockley et al.
2009/0182266 A1 7/2009 Gordon et al.
2010/0069825 A1 3/2010 Raney
2010/0118266 A1 5/2010 Nixon
2010/0287127 A1 11/2010 Claus et al.
2011/0112472 A1 5/2011 Jacobson et al.
2011/0144641 A1 6/2011 Dimalanta, Jr. et al.
2011/0313280 A1 12/2011 Govari et al.
2012/0209303 A1 8/2012 Frankhouser et al.
2012/0232466 A1 9/2012 Kuebler et al.
2013/0211435 A1 8/2013 Boukhny et al.
2014/0018724 A1 1/2014 Staggs
2014/0114296 A1 4/2014 Woodley et al.
2014/0257172 A1 9/2014 Yalamanchili
2014/0316254 A1 10/2014 Eversull et al.
2014/0323953 A1 10/2014 Sorensen et al.
2015/0045806 A1 2/2015 Urich et al.
2015/0073816 A1 3/2015 Ha et al.
2015/0148615 A1 5/2015 Brennan et al.
2015/0216726 A1 8/2015 Kadziauskas et al.
2016/0175543 A1 6/2016 Frankhouser et al.
2018/0028359 A1 2/2018 Gordon et al.
2018/0092555 A1 4/2018 Script
2018/0207330 A1 7/2018 Ovchinnikov et al.
2018/0318131 A1 11/2018 Boukhny et al.
2019/0201037 A1 7/2019 Houser et al.
2019/0274748 A1 9/2019 Danziger et al.
2020/0107958 A1 4/2020 Wong et al.
2020/0309760 A1* 10/2020 Durant ................ G01N 27/028
2021/0045918 A1 2/2021 Raney
2021/0196515 A1 7/2021 Urich
2021/0361481 A1 11/2021 Gliner et al.
2021/0401623 A1 12/2021 Zhang et al.
2022/0008251 A1 1/2022 Govari et al.
2022/0192876 A1 6/2022 Algawi et al.
2022/0192878 A1* 6/2022 Algawi ............... A61F 9/00745
2022/0313489 A1 10/2022 Hajishah et al.
2023/0039808 A1 2/2023 Govari et al.
2023/0043082 A1 2/2023 Govari et al.
2023/0210692 A1* 7/2023 Casutt ................ A61F 9/00745 604/22
2023/0218438 A1* 7/2023 Nahum ............... A61F 9/00745 606/107
2023/0285189 A1 9/2023 Govari
2023/0320897 A1 10/2023 Hajishah et al.
2024/0099884 A1 3/2024 Govari et al.
2024/0197173 A1* 6/2024 Kok ...................... A61B 34/25

FOREIGN PATENT DOCUMENTS

EP 0956840 A2 11/1999
EP 0776643 B1 8/2003
EP 1935383 A1 6/2008
EP 1765190 B1 7/2008
EP 1743309 B1 10/2011
EP 3448235 A2 3/2019
JP 4126304 B2 5/2008
WO 9211814 A1 7/1992
WO 2008016870 A2 2/2008
WO 2010014937 A1 2/2010
WO 2016122790 A1 8/2016
WO 2019069201 A1 4/2019
WO 2021119616 A1 6/2021
WO 2023017334 A1 2/2023

OTHER PUBLICATIONS

U.S. Appl. No. 17/357,587, titled, "Accurate Irrigation Rate Measurment System and Method," filed Jun. 24, 2021.
Co-pending U.S. Appl. No. 62/692,768, filed Jun. 29, 2018, 191 pages.

* cited by examiner

FIG. 5

| Name | Deviation from Cataract | Deviation from Cortex | Deviation from Capsule | Deviation from Water | Classification | Confidence |
|---|---|---|---|---|---|---|
| 1 | 14048.36536 | 38244.98965 | 44991.94866 | 45088.96416 | Cataract | 0.90133 |
| 2 | 18859.30242 | 43804.9963 | 50190.60912 | 49306.46151 | Cataract | 0.8837 |
| 3 | 9125.756812 | 21897.918 | 27863.98076 | 26333.48996 | Cataract | 0.89292 |
| 4 | 11191.07846 | 22874.83112 | 28459.41827 | 26734.74179 | Cataract | 0.87462 |
| 5 | 11937.65779 | 22728.27877 | 27814.16531 | 26091.04021 | Cataract | 0.86522 |
| 6 | 8234.234025 | 17667.22779 | 24132.40292 | 23833.35257 | Cataract | 0.88853 |
| 7 | 14677.71195 | 11270.30291 | 17482.26415 | 17478.40318 | Cortex | 0.81496 |
| 8 | 11481.74621 | 14415.23742 | 20931.28545 | 21117.32838 | Cataract | 0.83102 |
| 9 | 14264.07167 | 17300.63661 | 22100.32766 | 20373.05349 | Cataract | 0.80734 |
| 10 | 12518.67499 | 17618.76723 | 22862.65844 | 21328.7599 | Cataract | 0.83158 |
| 11 | 15057.95485 | 16989.79907 | 21657.98052 | 19907.3466 | Cataract | 0.79544 |
| 12 | 10852.66732 | 24233.23276 | 29596.74993 | 28037.39326 | Cataract | 0.88295 |
| 13 | 15572.08259 | 13183.91714 | 18218.28536 | 16791.12589 | Cortex | 0.79324 |
| 14 | 14623.82962 | 16645.80128 | 21395.64478 | 19686.84346 | Cataract | 0.79788 |
| 15 | 19719.44723 | 13097.6976 | 16600.4321 | 14575.99397 | Cortex | 0.79533 |

FIG. 12

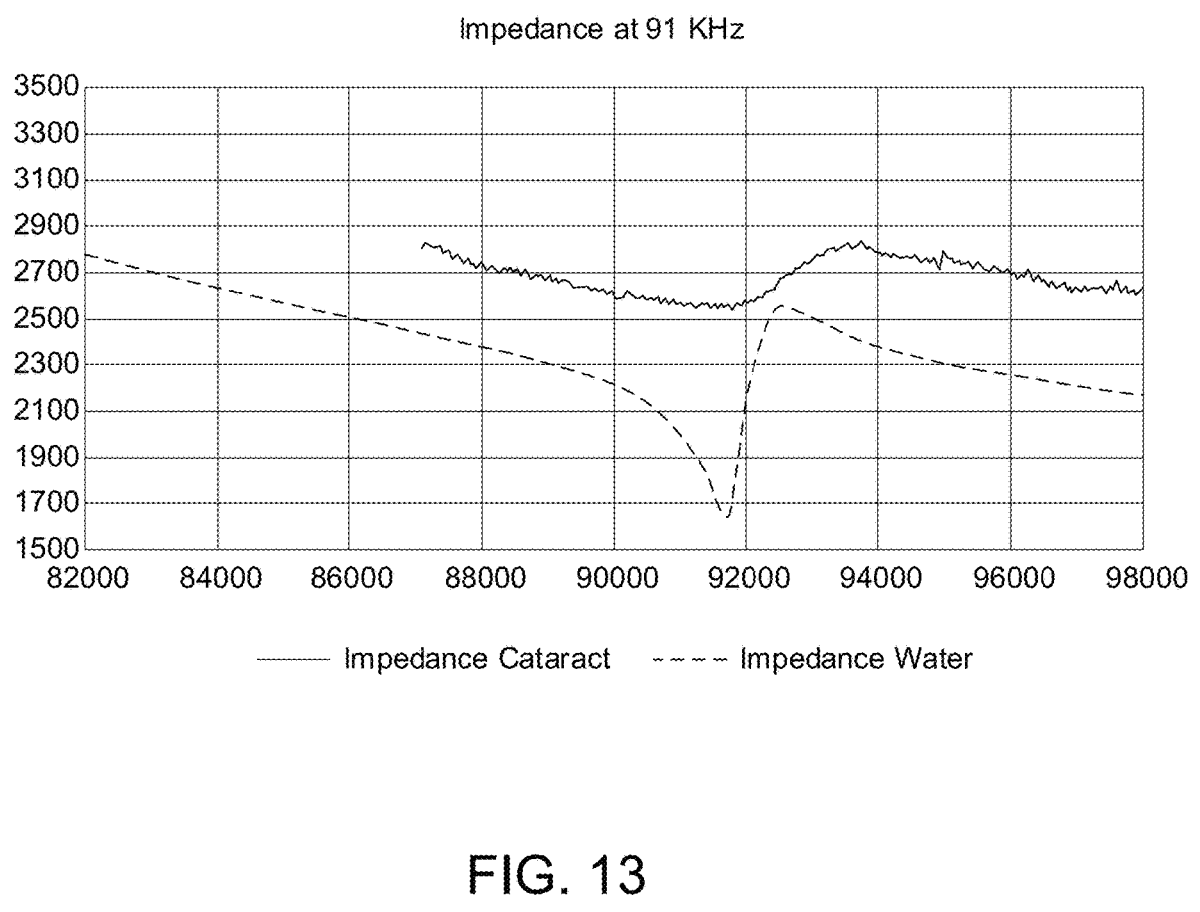

Impedance at 91 KHz 3500
3300
3100
2900
2700
2500
2300
2100
1900
1700
1500
82000 84000 86000 88000 90000 92000 94000 96000 98000

Impedance Cataract ---- Impedance Water

FIG. 13

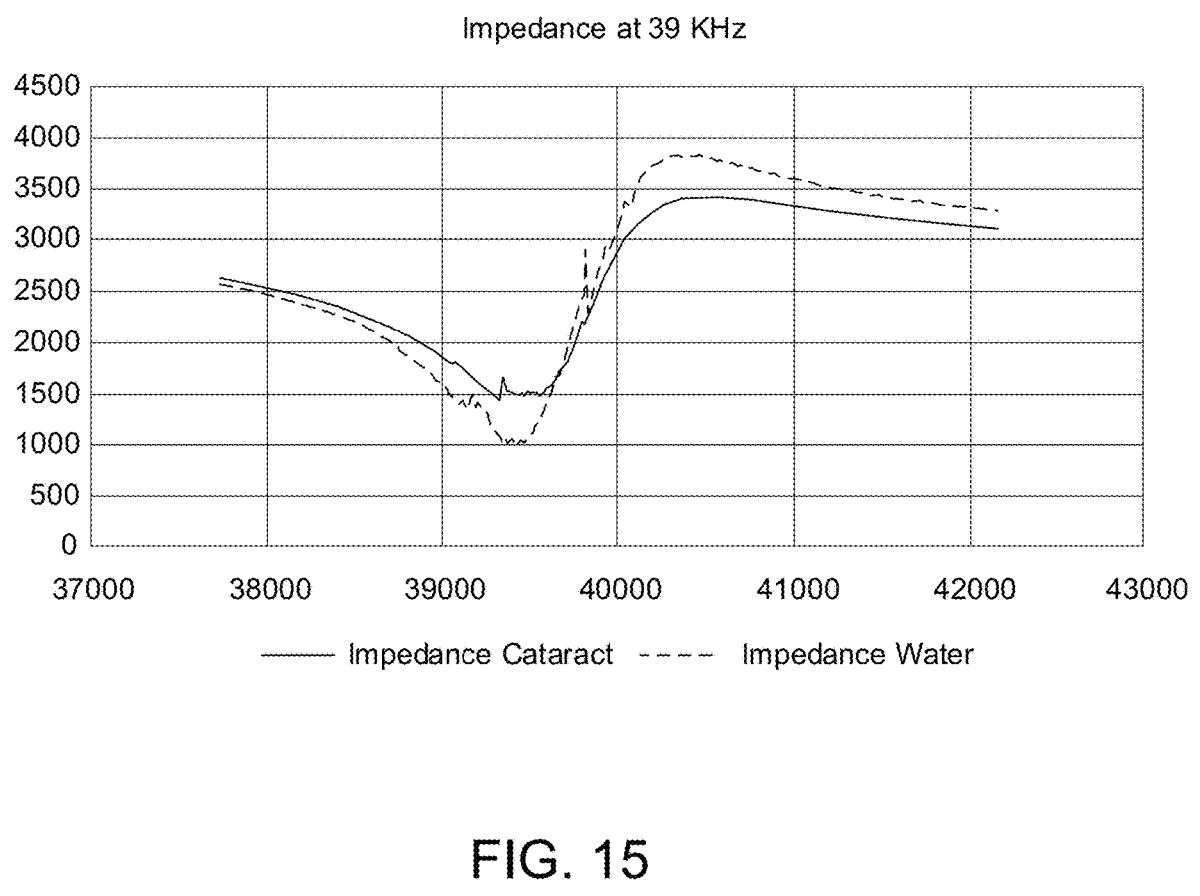

Impedance at 39 KHz 4500
4000
3500
3000
2500
2000
1500
1000
500
0

37000 38000 39000 40000 41000 42000 43000

Impedance Cataract
Impedance Water

FIG. 15

METHOD AND SYSTEM FOR CATARACT TISSUE SENSING

FIELD OF INVENTION

This invention generally relates to surgical devices used in ocular surgery and more specifically to hand-held ultrasonic devices for use in phacoemulsification procedures.

BACKGROUND

One objective of cataract surgery is to remove a patient's clouded lens by fragmenting and emulsifying the lens and extracting the emulsified lens so that it can be replaced with an artificial lens. This process, phacoemulsification, is accomplished through the use of an ultrasonic handpiece. The ultrasonic handpiece includes a needle having a distal end with an aspiration port connected via tubing to a phacoemulsification console. After the needle is inserted into a patient's eye, vacuum pressure induced within the aspiration tubing causes material within the eye to be aspirated through the needle. The ultrasonic handpiece is also fitted with irrigation tubing through which sterile irrigation fluid travels from the console and into the eye, replacing volumes of fluid and material in the eye that are lost due to aspiration and leakage. The distal end of the needle is configured to vibrate at an ultrasonic frequency, which, when in contact with tissue of the eye, may cut through and break apart the cataract into smaller pieces that can more easily be aspirated through tubing within the handpiece.

In the anatomy of the eye, the lens is separated from the interior of the eye by the lens capsule. The lens capsule may need to remain intact because it forms a barrier between the aqueous chamber and the vitreous chamber of the eye. If the lens capsule is broken, it must be repaired, which may lengthen and complicate the procedure.

Using existing methods for phacoemulsification, the lens capsule may become damaged due to human error. For example, a surgeon may cut through the lens capsule if the tip of the ultrasonic handpiece accidentally touches the lens capsule while ultrasonic power is activated. This may occur because the lens capsule sits directly behind the lens, and the surgeon may inadvertently continue to supply ultrasonic power after the cataract occlusion has been broken up and aspirated. Ideally, the surgeon would activate ultrasonic power only when the tip of the handpiece is touching the cataract.

SUMMARY

Systems and methods for sensing tissue in a phacoemulsification procedure are provided herein. A method may include generating a sensing signal through a frequency range centered at a local resonant frequency of an ultrasonic handpiece and measuring impedance characteristics of the signal at a distal end of a needle of an ultrasonic handpiece. A method may further include comparing the measured impedance characteristics of the generated sensing signal with one or more stored impedance profiles. A method may further include classifying, based on the comparison between the measured impedance characteristics and the stored one or more impedance profiles, a medium contacting the distal end of the needle of the ultrasonic handpiece. A method may further include controlling an output of the ultrasonic handpiece based on the classification of the medium contacting the distal end of the needle of the ultrasonic handpiece.

BRIEF DESCRIPTION OF THE DRAWINGS

FIG. 5 is an example of a two-dimensional representation of an impedance profile generated when a needle is in contact with air;

FIG. 12 is a table illustrating an example of deviation data calculated across multiple sets of measurement data;

FIGS. 13 and 14, respectively illustrate impedance magnitude and impedance phase data measured within a frequency band centered around 91 KHz;

FIGS. 15 and 16 respectively illustrate impedance magnitude and impedance phase data measured within a frequency band centered around 39 KHz;

DETAILED DESCRIPTION OF THE PREFERRED EXAMPLES(S)

In an ideal phacoemulsification cataract surgery, ultrasonic power is activated only when the tip of the handpiece is touching the cataract to avoid cutting through tissue in the eye other than the cataract. To accomplish this, impedance measurements, taken by sweeping a low-power signal across a frequency band and measuring a response signal at the tip of the needle, may be used to classify the material that the tip of the device is in contact with.

Some methods may evaluate impedance measurement data in combination with other metrics, such as the aspiration rate (cc/min) and vacuum pressure (mmHg) of the aspiration line of the phacoemulsification handpiece and the aspiration tube coupled with the handpiece. If the tip of the device is obstructed (e.g., by a large piece of cataract), the aspiration levels may drop close to zero and the vacuum pressure may increase significantly. Such aspiration and vacuum parameters may be used alone or in combination with impedance measurements to detect occlusion; hence, some solutions may use a combination of ultrasonic impedance analysis, aspiration, and pressure monitoring to identify when the tip is blocked, and if it is blocked by a piece of cataract, or by other tissue in the eye.

In some methods, ultrasonic power may be activated only when it has been determined that the tip is touching cataract tissue, thus preventing the surgeon from mistakenly cutting into the lens capsule. While impedance measurement data alone is sufficient to identify if a cataract is present at the tip, some methods may involve first measuring the vacuum pressure and aspiration rate to determine when an occlusion occurs at the tip. The impedance profile may then be used to confirm that this occlusion is caused by a cataract. In some methods, ultrasonic power may be activated only when it has been indicated from the ultrasonic impedance profile, and possibly vacuum pressure and/or aspiration rate, that the tip of the device is touching cataract tissue.

Figure 1:
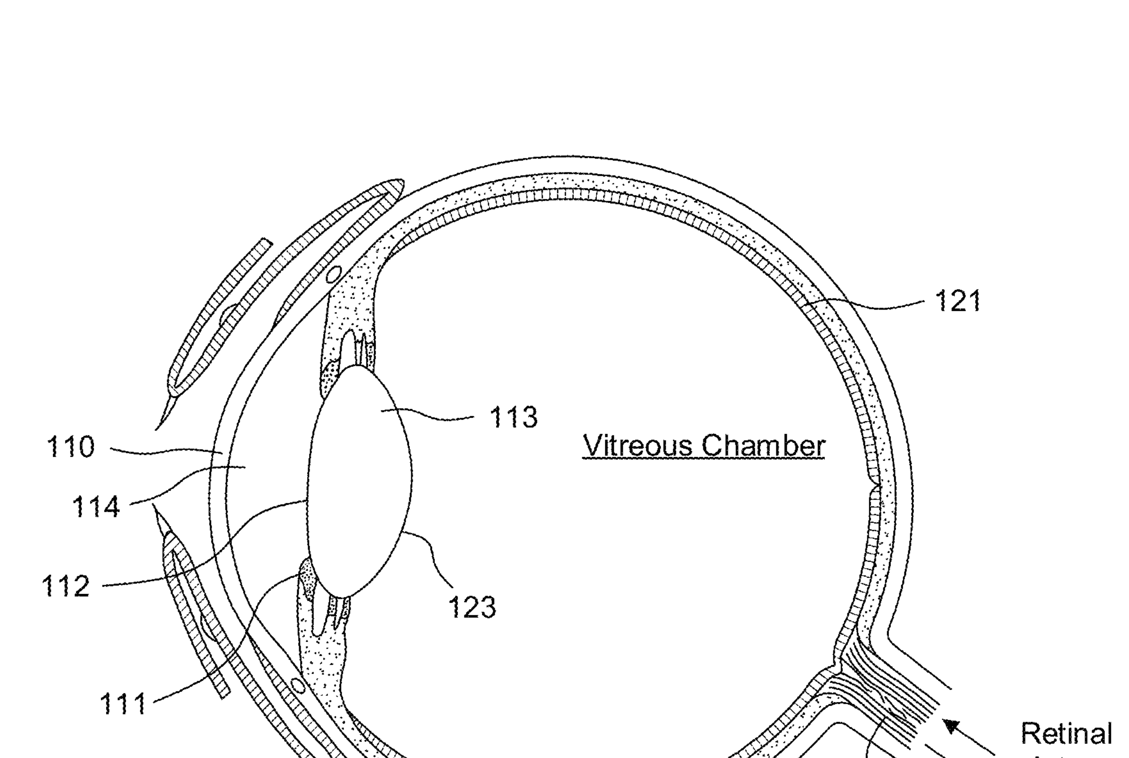
FIG. 1 is an anatomical illustration of a human eye.

FIG. 1 is an anatomical illustration of a human eye. An anterior portion of a human eye 100 includes the cornea 110, an aqueous chamber 114, the iris 111, the pupil 112 and the crystalline lens 113 (also referred to herein as the lens 113). The aqueous chamber 114 may also be referred to as the anterior chamber in some cases. A posterior portion of the human eye 100 includes the vitreous chamber 120, which includes the retina 121, the optic nerve 122, and is separated from the lens 113 of the aqueous chamber 114 by the lens capsule 123. The cornea 110 functions to focus light entering the eye from external sources. The iris 111 constricts or dilates the pupil 112 to control the amount of light that enters the lens 113 and reaches the retina 121. The lens 113 refracts light passing through the pupil 112 onto the retina 121, which triggers nerve impulses that enable visual perception.

Figure 2:
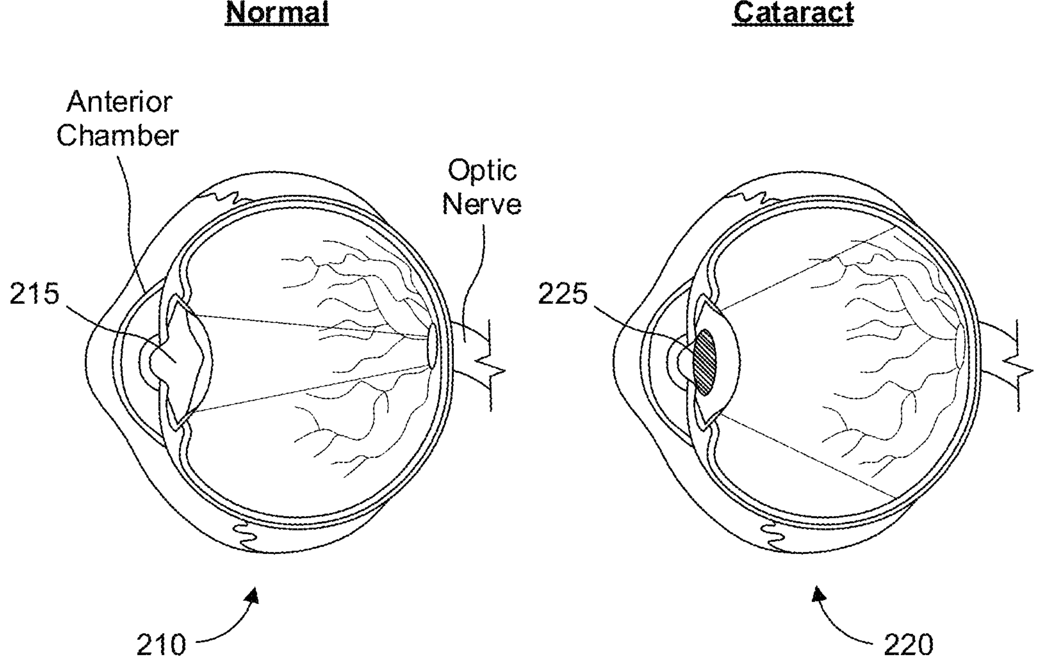
FIG. 2 illustrates a comparison between a healthy human eye having a clear lens and an eye in which a cataract has formed.

FIG. 2 illustrates a comparison between a healthy human eye having a clear lens and an eye in which a cataract has formed. As shown in FIG. 2, a healthy eye 210 may have a lens 215 that is free from cataracts. When in a healthy state, the clear lens 215 may be transparent such that light is able to be focused through the lens without deleterious effect to visual acuity. On the other hand, an eye 220 having a lens 225 in which a cataract has formed may result in vision that is partially or fully impaired. A cataract may develop as an opaque area in the lens 225, which may appear as a clouded area. In some instances, a cataract may develop as a sclerotic (i.e., a rigid) formation that affects the ability of the lens to focus.

Figure 3:
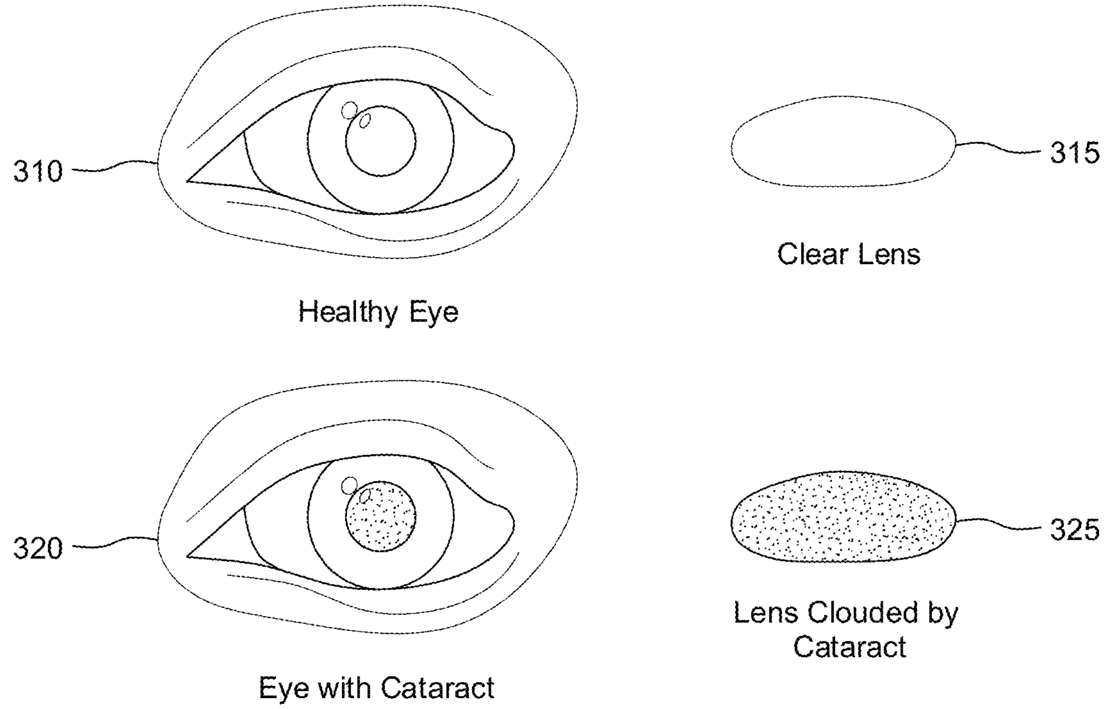
FIG. 3 illustrates a comparison between the operation of a lens of a normal human eye and the operation of a lens of an eye in which a cataract has formed.

FIG. 3 illustrates a comparison between the operation of a lens of a normal human eye 310 and the operation of a lens of an eye 320 in which a cataract 325 has formed. As shown in FIG. 3, the normal eye 310 may have a lens 315 that is not affected by a cataract. Light passes through the cornea, is restricted by the pupil and iris, and is refracted through the lens. The refracted light is focused into a two-dimensional image, which strikes photoreceptors of the retina and triggers nerve impulses to the brain via the optic nerve. As shown in FIG. 3, an eye 320 in which a cataract 325 has developed may have difficulty focusing light onto the retina. For example, the two-dimensional image may be subject to various aberrations that cause scattering of the image or glare, for example. Such scattering may result in partial or complete blindness depending on the severity of the aberration.

Cataracts may be removed through various types of surgical procedures. A phacoemulsification procedure is one type of procedure by which a patient's clouded lens may be broken up and removed from the eye (e.g., aspirated through a vacuum), before being replaced with an artificial lens. The removal process may be accomplished through the use of an ultrasonic handpiece equipped with an ultrasonic tip/needle. Ultrasonic power applied through the handpiece may induce high-frequency movements of the tip that cut through the affected lens. Once broken into smaller pieces, the lens may be aspirated out of the eye via the handpiece.

This lens capsule needs to remain intact because it forms a barrier between the aqueous chamber and the vitreous chamber of the eye. If the lens capsule is broken, the surgeon must remediate the damaged caused, which adds time and difficulty to the surgery. Surgeons will sometimes cut through the lens capsule because they accidentally touch it while ultrasonic power is activated. This occurs because the lens capsule sits directly behind the lens, and the surgeon may continue to supply ultrasonic power (by pressing on a foot pedal) after the cataract occlusion has been broken up and aspirated. In an ideal surgery, the surgeon would have the ultrasonic power activated only when the tip of the handpiece is touching the cataract.

Figure 4:
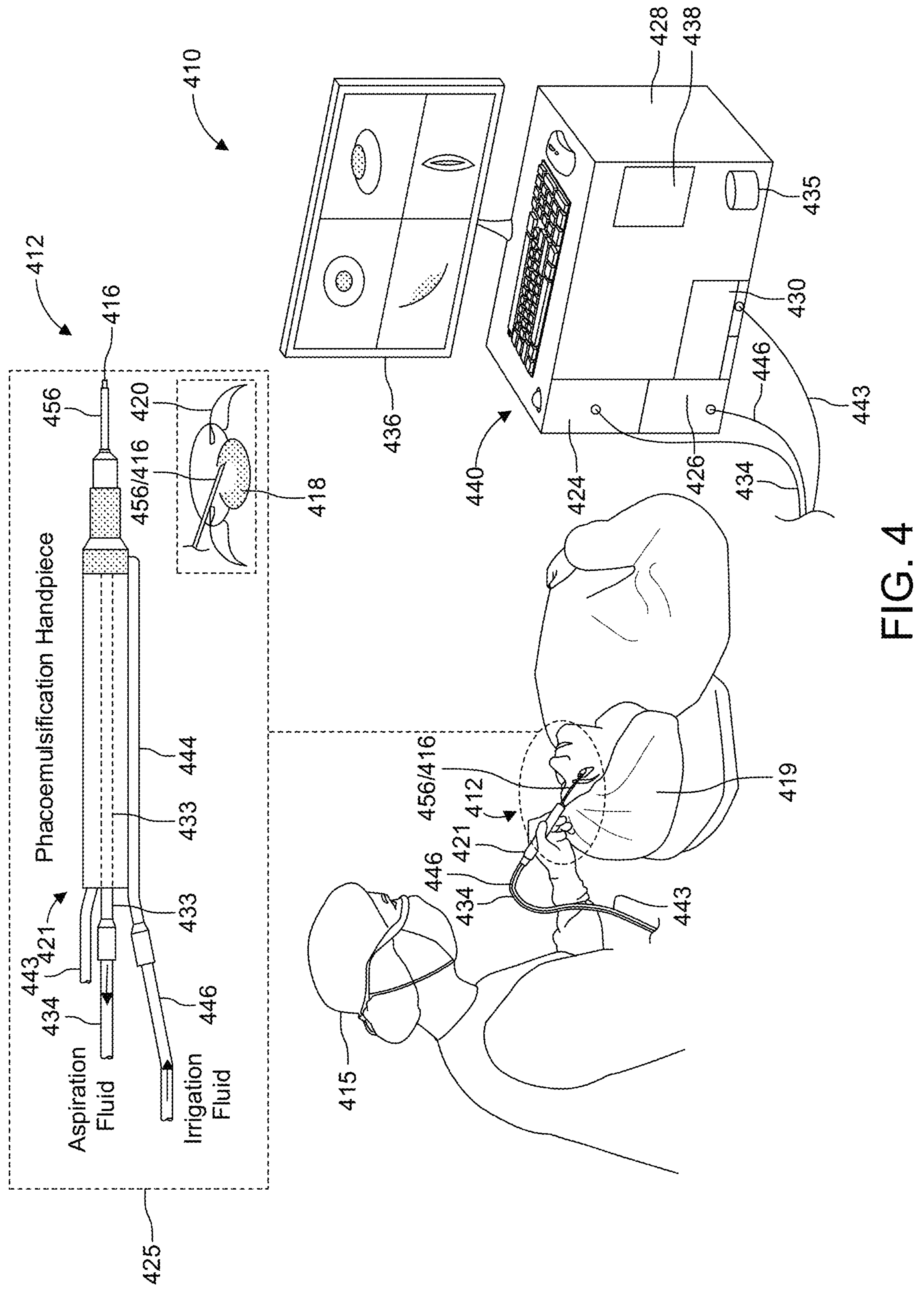
FIG. 4 is a schematic, pictorial illustration of an example of a phacoemulsification system.

FIG. 4 is a schematic, pictorial illustration of an example of a phacoemulsification system 410. In some examples, system 410 comprises a hand-held device, in the present example a phacoemulsification probe, also referred to herein as a probe 412 or as an ultrasonic handpiece for brevity.

The pictorial inset 425 of FIG. 4 shows details of the probe 412. In some examples, probe 412 includes a needle 416 and a coaxial irrigation sleeve 456 that at least partially surrounds needle 416 and creates a fluid pathway between the external wall of the needle and the internal wall of the irrigation sleeve.

In some examples, irrigation sleeve 456 may have one or more side ports at or near the distal end, so as to allow irrigation fluid to flow toward the distal end of probe 412 through the fluid pathway and out of the port(s). In such examples, the irrigation fluid is configured to cool the distal end of probe 412, and particularly, needle 416, which is heated when one or more piezoelectric crystals (not shown; described below) of probe 412 are operating.

Note that needle 416 is hollow and is configured to aspirate fluids from a patient's eye during a phacoemulsification procedure. In the present example, needle 416 is configured to draw at least eye fluid (e.g., natural eye fluid, irrigation fluid and lens material described below) from the patient's eye to an aspiration channel 433 described below.

In some examples, needle 416 or another suitable element of probe 412 may be able to transfer irrigation fluid from an irrigation channel 444 to the patient's eye.

In some examples, needle 416 is configured for insertion into a lens capsule 418 of an eye 420 of a patient 419 by a physician 415, so as to remove a cataract. In the present example, needle 416 and irrigation sleeve 456 are shown in the pictorial inset 425 as a straight object, but in other embodiments any other suitable type of needle may be used with probe 412. For example, a curved or bent tip needle commercially available, for example, from Johnson & Johnson Surgical Vision, Inc., Irvine, CA, USA.

Reference is now made back to the general view of FIG. 4. In some examples, during the aforementioned phacoemulsification procedure, a pumping sub-system 424 provided by a console 428 of system 410, is configured to pump irrigation fluid, such as a balanced salt solution, from an irrigation reservoir (not shown), via an irrigation tube 434 and irrigation channel 444 of probe 412, to irrigation sleeve 456 for irrigating the patient's eye. In other examples, pumping sub-system 424 may be coupled with or replaced by a gravity fed irrigation source such as a balanced salt solution bottle/bag.

In some examples, during the phacoemulsification procedure, physician 415 uses the aforementioned piezoelectric crystals of probe 412 to apply vibrations to needle 416 for emulsifying the lens of patient's eye 420. The irrigation fluid is instilled into eye 420 (as described above) during the emulsification, so as to: (i) compensate for eye fluid aspirated from eye 420 (described in detail below) for maintaining constant intraocular pressure (IOP) in eye 420, and (ii) control a constant temperature in eye 420 (e.g., by dissipating heat generated by the vibration of needle 416) during the procedure. Note that during the emulsification of the lens of eye 420, eye fluid comprises natural eye fluid, irrigation fluid, and lens material (e.g., the emulsified parts of the cataract), which is aspirated using probe 412 as described herein.

In some examples, the eye fluid is being aspirated, via hollow needle 416 and aspiration channel 433 of probe 412, and via an aspiration tube 434, to a collection receptacle (not shown) using a pumping sub-system 426 of console 428. In such examples, aspiration tube 434 is coupled with and running between aspiration channel 433 of probe 412 and pumping sub-system 426 of console 428.

In other examples, pumping sub-systems 424 and 426 may have any other suitable configuration in a fluidics cartridge/cassette (not shown) or in console 428 of system 410. For example, both pumping sub-systems 424 and 426 may be co-packaged, and/or at least one of pumping sub-systems 424 and 426 (typically sub-system 424) may use other pumping techniques, such as being coupled with or replaced by the aforementioned gravity fed irrigation source.

In the example of probe 412 shown in the pictorial inset 425 of FIG. 4, irrigation channel 444 and irrigation tube 446 are not aligned with needle 416, so as to have direct flow of the irrigation tube into a patient's eye. In this configuration, aspiration channel 433 and aspiration tube 434 are fluidly connected to needle 416 and aligned (i.e., facing). In alternative examples, probe 412 may have a different configuration in which the positions of the channels (and respective tubes) are exchanged. In such examples, irrigation channel 444 and irrigation tube 446 are aligned with needle 416 (instead of the position of aspiration channel 433 and aspiration tube 434 shown in pictorial inset 425), In other examples, probe 412 may have any other suitable arrangement of the aforementioned channels and respective tubes.

In some examples, probe 412 includes additional elements (not shown), such as but not limited to one or more piezoelectric crystals coupled with a horn for driving vibration of needle 416. The piezoelectric crystal(s) is configured to vibrate needle 416 in a resonant vibration mode. The vibration of needle 416 is used for breaking the aforementioned cataract into small pieces, e.g., constitutes the aforementioned lens material, during the phacoemulsification procedure.

In some examples, console 428 comprises a piezoelectric drive module 430, coupled with the one or more piezoelectric crystals, using electrical wiring running in a cable 443. Drive module 430 is controlled by a processor 438 and conveys processor-controlled driving signals via cable 443 to, for example, maintain needle 416 at maximal vibration amplitude. The drive module may be implemented in hardware or software, for example, in a proportional-integral-derivative (PID) control architecture.

In some examples, processor 438 is configured to receive user-based commands via a user interface 440, which may include setting a vibration mode and/or frequency of the piezoelectric crystal(s) and setting or adjusting an irrigation and/or aspiration rate of pumping sub-systems 424 and 426. In an example, user interface 440 and a display 436 may be combined as a single touch screen graphical user interface. In an example, physician 415 uses a foot pedal (not shown) as a means of control. Additionally, or alternatively, processor 438 may receive the user-based commands from controls located in a handle 421 of probe 412. In some examples, processor 438 may include a general-purpose processor, which is programmed in software to carry out the functions described herein. Some or all of the functions of processor 438 may be combined in a single physical component or, alternatively, implemented using multiple physical components. These physical components may comprise hard-wired or programmable devices, or a combination thereof.

In some examples, at least some of the functions of processor 438 may be carried out using suitable software stored in a memory 435. This software may be downloaded to a device in electronic form, over a network, for example. Alternatively, or additionally, the software may be stored in tangible, non-transitory computer-readable storage media, such as optical, magnetic, or electronic memory.

In some examples, system 410 and in particular console 428 and probe 412, may comprise additional elements which are omitted for the sake of conceptual clarity. For example, physician 415 typically performs the procedure using a stereo-microscope and/or magnifying glasses and/or augmented/virtual reality head mount display (HMD), neither of which are shown. Physician 415 may use other surgical tools in addition to probe 412, which are also not shown in order to maintain clarity and simplicity of the present disclosure.

This particular configuration of system 410 is shown by way of example, in order to illustrate certain problems that are addressed by examples of the present invention and to demonstrate the application of these examples in enhancing the performance of such a phacoemulsification system. Examples of the present invention, however, are by no means limited to this specific sort of example phacoemulsification system, and the principles described herein may similarly be applied to other sorts of phacoemulsification or other suitable types of surgical systems.

Methods and systems described herein may incorporate functionality enabling sensing or detection of different media, namely cataract and lens capsule tissue. Such sensing or detection may enable automatic deactivation or activation of ultrasonic power, thereby reducing the possibility of inadvertent application of ultrasonic power to the lens capsule or other tissues. In some examples, automatic deactivation of ultrasonic power may be performed when it is determined that the tip of the handpiece is not in contact with cataract tissue. In some examples, automatic activation of ultrasonic power may be performed when it is determined that the tip of the handpiece is in contact with cataract tissue.

To enable sensing or detection of various media, a signal is delivered to the ultrasonic handpiece and various aspects of the signal observed at the handpiece are measured. The signal delivered to the handpiece may be used for sensing, for example, during surgical operation of the handpiece, or outside of a surgical operation such as during a setup, calibration, or troubleshooting procedure. Sensing may be performed at the same time during which ultrasonic power is delivered to the handpiece, at a time during which ultrasonic power is not delivered to the handpiece, or both.

In some examples, the signal delivered to the handpiece may be a low-power signal (e.g., less than 5 Watts). The signal used for sensing may be a sub-therapeutic signal, which may be a signal providing a less-than-effective therapeutic result, or a signal delivered at a power level less than that which is required to emulsify or decimate tissue. The signal may be delivered to the handpiece (e.g., swept) across multiple different frequencies of a band. The band in which the signals are swept may reside within a larger frequency range that is implementation dependent (e.g., dependent upon the ultrasonic frequency capabilities of the ultrasonic handpiece). For instance, in some implementations, signals may be swept across a band of frequencies located within a recommended frequency range between 0-200 KHz. The band of frequencies may be centered around a local resonant frequency. For instance, a signal swept within a 92 KHz band that has a width of 5 KHz may be swept at frequencies between 89 and 94 KHz.

The width of the band in which signals are swept may vary depending upon the implementation. For example, the band width may be less than 1 KHz, between 1 and 5 KHz, or greater than 5 KHz. The frequency range in which the band is located may range, for example, between 5-10 KHz, 5-20 KHz, 5-200 KHz, though the frequency range may conceivably include any frequencies within which an ultrasonic handpiece is capable of operation.

A local resonant frequency at which the signal is swept may be the same frequency at which the ultrasonic handpiece is driven to excite a longitudinal mode of the needle. A longitudinal mode refers to a back-and-forth movement of the ultrasonic tip/needle along the longitudinal axis of the handpiece and is differentiated from a torsional mode, which refers to a to and fro motion or rotations about the longitudinal axis, elliptical movement of the needle, or from a lateral mode, which may refer to side-to-side movement of the needle. In other examples, selected frequency or frequency range may be the same as a local resonant frequency that excites any one or more of the modes.

Real-time measurement of the signal at the distal end of the needle is performed to enable classification of the medium contacting the needle. Characteristics of the signal that are measured may include, but are not limited to, frequency, impedance phase, and/or impedance magnitude data. One or more of such characteristics may vary based on the material or medium contacting the needle. Measurement data may be collected in a time instance or over a time interval. The measurement data may be stored by the implementing system. The measurement data may be graphically represented in two dimensions (e.g., considering two of the measured signal characteristics, or considering one of the measured signal characteristics plus time). In an example, when considering frequency, impedance phase, and impedance phase the data may be graphically represented in three dimensions, for instance, such that each of the frequency, impedance phase, and impedance magnitude are plotted on different axes.

Measurement data that is collected while the needle is in contact with a given medium may be used to generate an impedance profile associated with such medium. For instance, data collected while the needle is in contact with cataract tissue may produce a unique data pattern. Unique data patterns may also be generated for other media such as water, viscoelastic, air, and other tissue such as the lens capsule and cortex. Graphically represented, the unique data patterns exhibit a distinctive curve.

Figure 5:
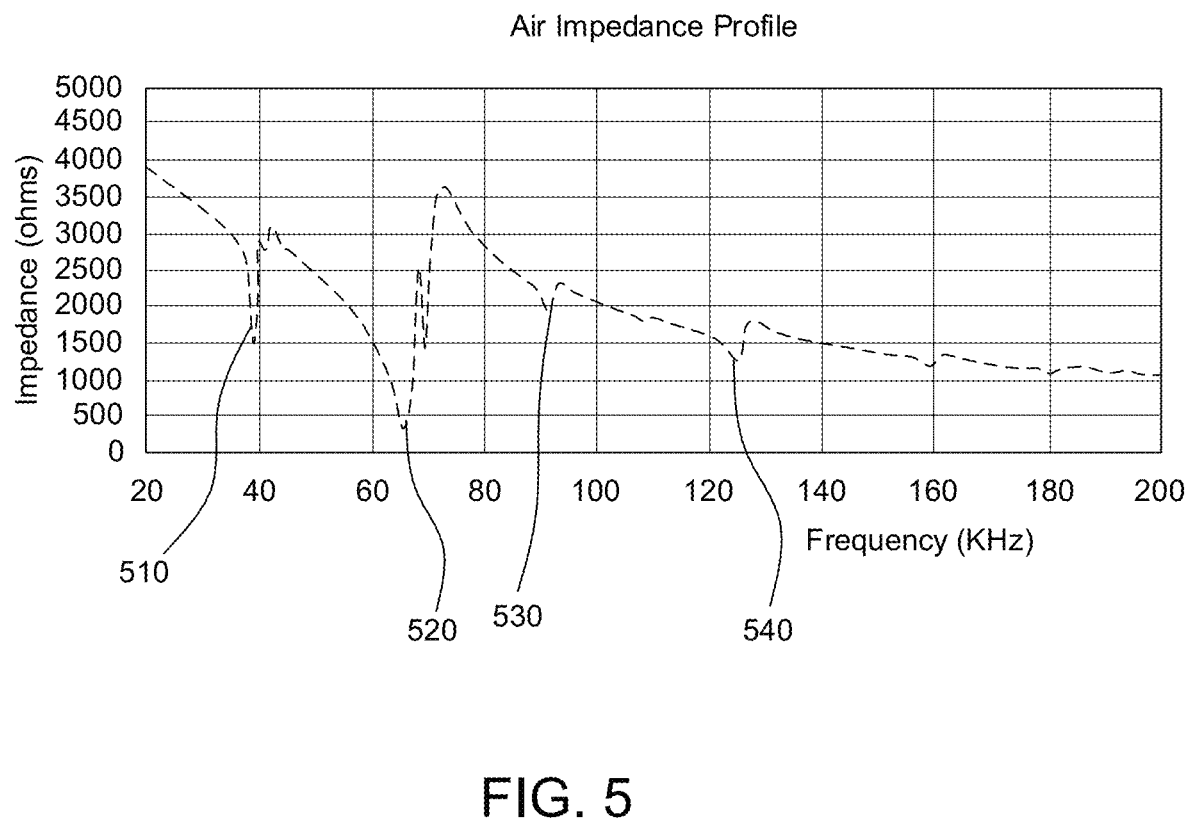

FIG. 5 is an example of a two-dimensional representation of an impedance profile generated when a needle is in contact with air. Substantially as described in paragraphs above, a signal is delivered to the needle at least over the frequency range of 20-200 KHz. Characteristics of the response signal observed at the needle are measured. As represented in FIG. 5, at least impedance and frequency data are captured. The graphical representation in FIG. 5 depicts the unique pattern exhibited by the impedance of the response signal observed at the needle as it remains in contact with the air. The behavior of the response signal at local resonant frequencies can be observed at the sharp peaks and valleys 510, 520, 530, and 540.

Figure 6:
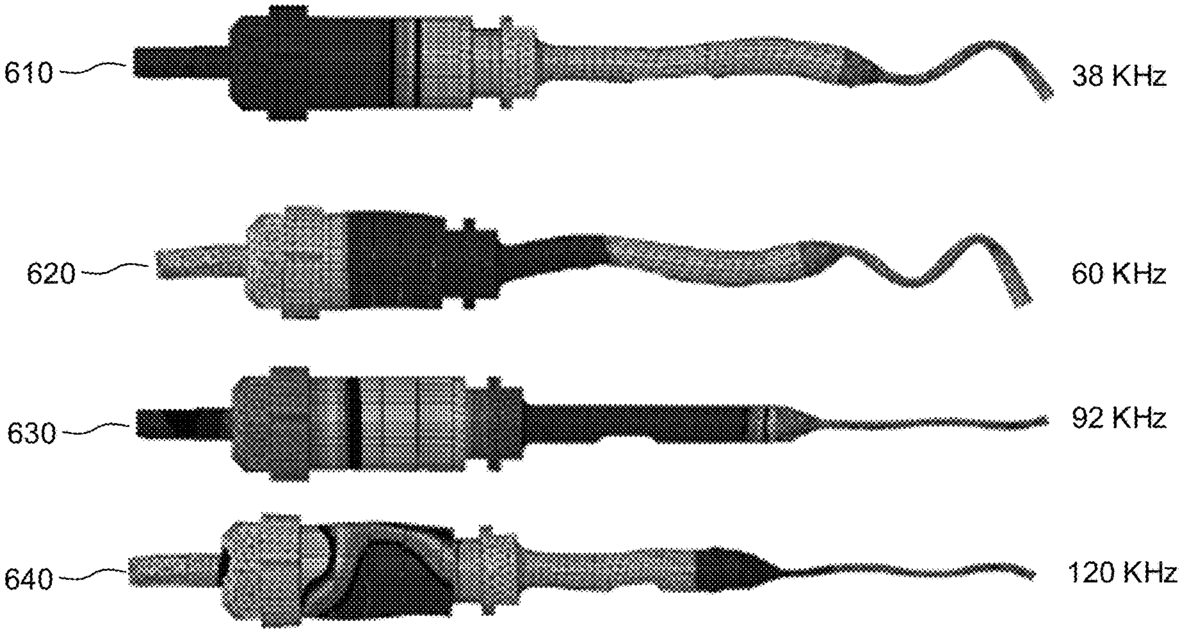
FIG. 6 is an illustration depicting finite element analysis (FEA) simulations of an ultrasonic handpiece.

FIG. 6 is an illustration depicting examples of finite element analysis (FEA) simulations of an ultrasonic handpiece. As shown in FIG. 6, illustrations 610, 620, 630, and 640 depict simulations of the ultrasonic handpiece in which the ultrasonic handpiece is driven at frequencies of 38 KHz, 60 KHz, 92 KHz, and 120 KHz. Each of the FEA simulation illustrations 610, 620, and 640 of the handpiece illustrates primarily torsional and/or lateral movement induced by the 38 KHz, 60 KHz, and 120 KHz oscillation, respectively. By contrast, illustration 630 portrays an FEA simulation of a 92 KHz resonant frequency that induces primarily longitudinal movement of the handpiece.

An implementing system may be pre-loaded with "master" profiles for relevant materials for classification. The master profiles may include measurement data gathered while the needle is in contact with known media. As described above, such measurement data may form unique data patterns that exhibit distinctive curves for each medium. The master profiles may be calibrated from measurement data observed across multiple frequency ranges and/or bands. For instance, measurement data for preparing a master profile for each medium may be captured across an entire frequency range from 0-200 KHz. In some examples, the measurement data may be captured across 5 KHz bands centered at local resonant frequencies for the ultrasonic handpiece, substantially as described above.

For generating the master profiles, the measurement data may be obtained from one or more of a wide range of resources. For instance, the measurement data may be gathered in a controlled laboratory setting where the needle is placed in contact with known materials. Examples of materials used for calibrating and/or testing the system may include ordinary tap water, air, and artificial cataract, capsule, and cortex tissue such as the Kitaro Eye artificial lens. It should be appreciated that any substance or model used to simulate the cataract may be chosen based on its efficacy in simulating behavior of the lens capsule during a phacoemulsification procedure. For instance, some models, such as the Kitaro Eye artificial lens, may effectively simulate behavior of tissues undergoing anterior capsulorhexis, or the removal of the anterior portion of the lens capsule. In some cases, animal models providing ocular tissue with impedance characteristics similar to human ocular tissue may be used.

In some examples, measurement data may be gathered in a clinical setting, such as during a phacoemulsification procedure in which the needle of the handpiece contacts air, liquids, and tissue of a human patient. For instance, the present invention may be implemented alongside a system for aggregating surgical data such that the aggregated measurements better approximate the average real-world impedance and frequency values for all patients.

Figure 7:
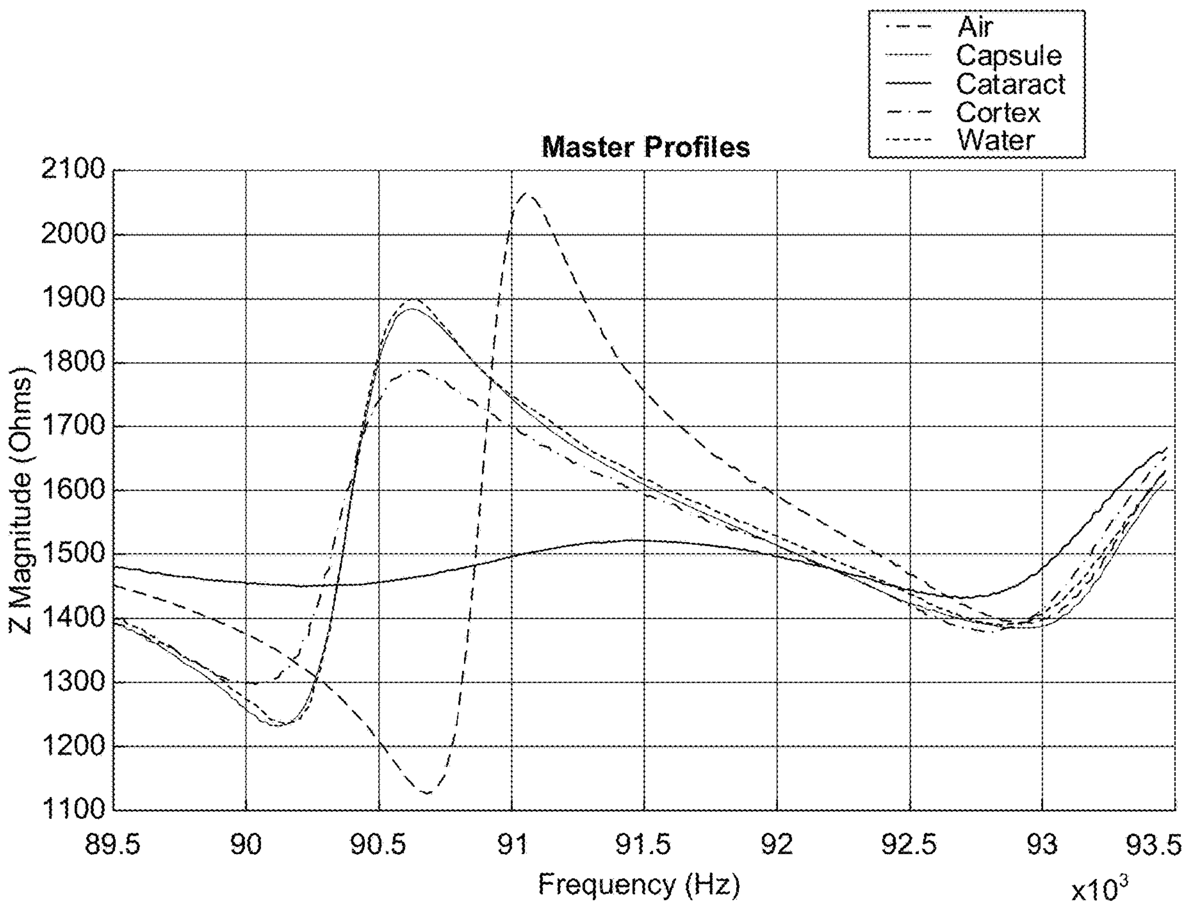
FIG. 7 is a plot illustrating frequency and impedance magnitude information, where frequency information is plotted along the x-axis and impedance magnitude ("Z magnitude") information is plotted along the y-axis.
Figure 8:
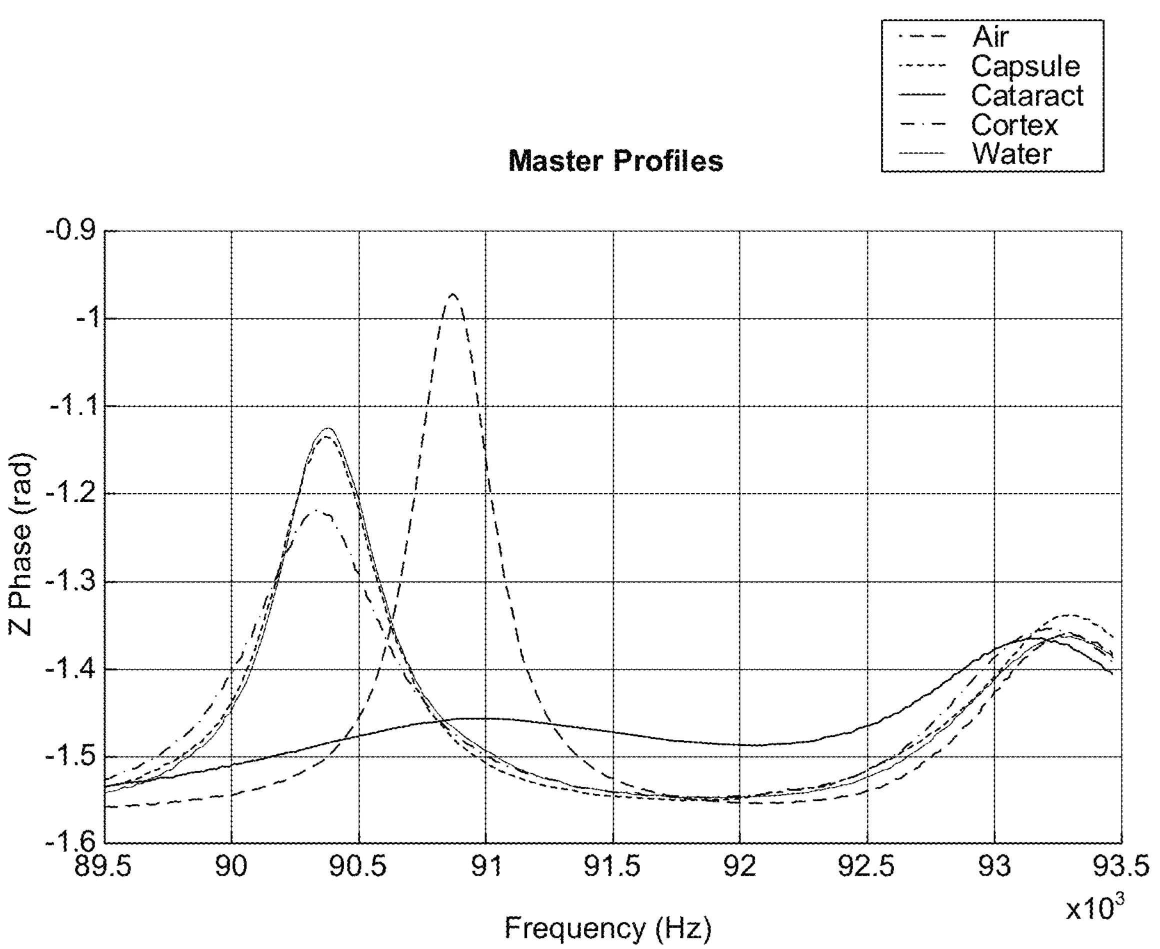
FIG. 8 is a plot illustrating frequency and impedance phase information, where frequency information is plotted along the x-axis and impedance phase ("Z Phase") information is plotted along the y-axis.
Figure 9:
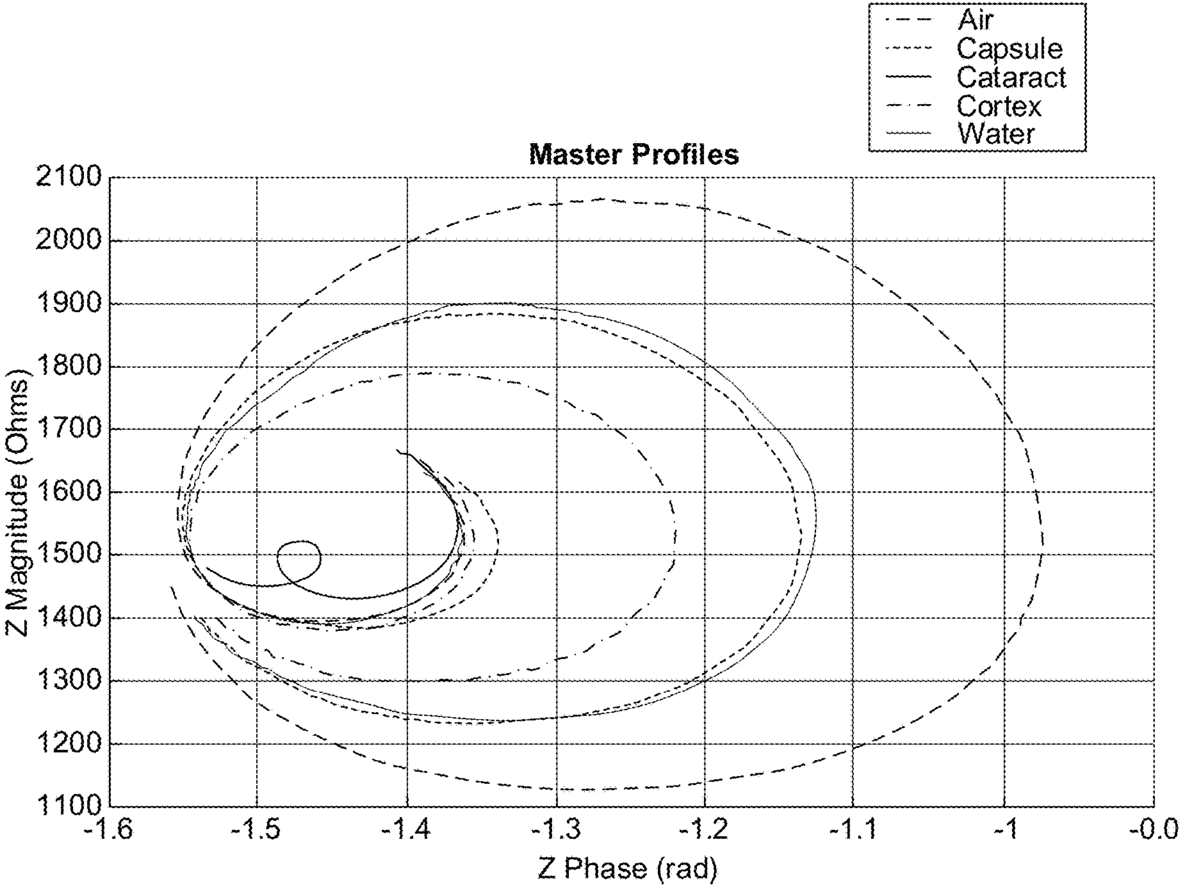
FIG. 9 is a plot illustrating impedance phase and magnitude information, where impedance phase information ("Z Phase") is plotted along the x-axis and impedance magnitude information is plotted along the y-axis.

FIGS. 7-9 illustrate examples of two-dimensional plots of measurement data master profiles for a range of media. As shown in FIGS. 7-9, each curve portrays impedance data corresponding to response signals observed at the needle while in contact, respectively, with air, lens capsule tissue, cataract, cortex, and water. In the examples shown in FIGS. 7-9, sensing signals are swept over a frequency band of ranging at least from 89.5 KHz to 93.5 KHz. FIG. 7 in particular is a plot illustrating frequency and impedance magnitude information, where frequency information is plotted along the x-axis and impedance magnitude ("Z magnitude") information is plotted along the y-axis. FIG. 8 is a plot illustrating frequency and impedance phase information, where frequency information is plotted along the x-axis and impedance phase ("Z Phase") information is plotted along the y-axis. FIG. 9 is a plot illustrating impedance phase and magnitude information, where impedance phase information ("Z Phase") is plotted along the x-axis and impedance magnitude information is plotted along the y-axis.

Figure 10:
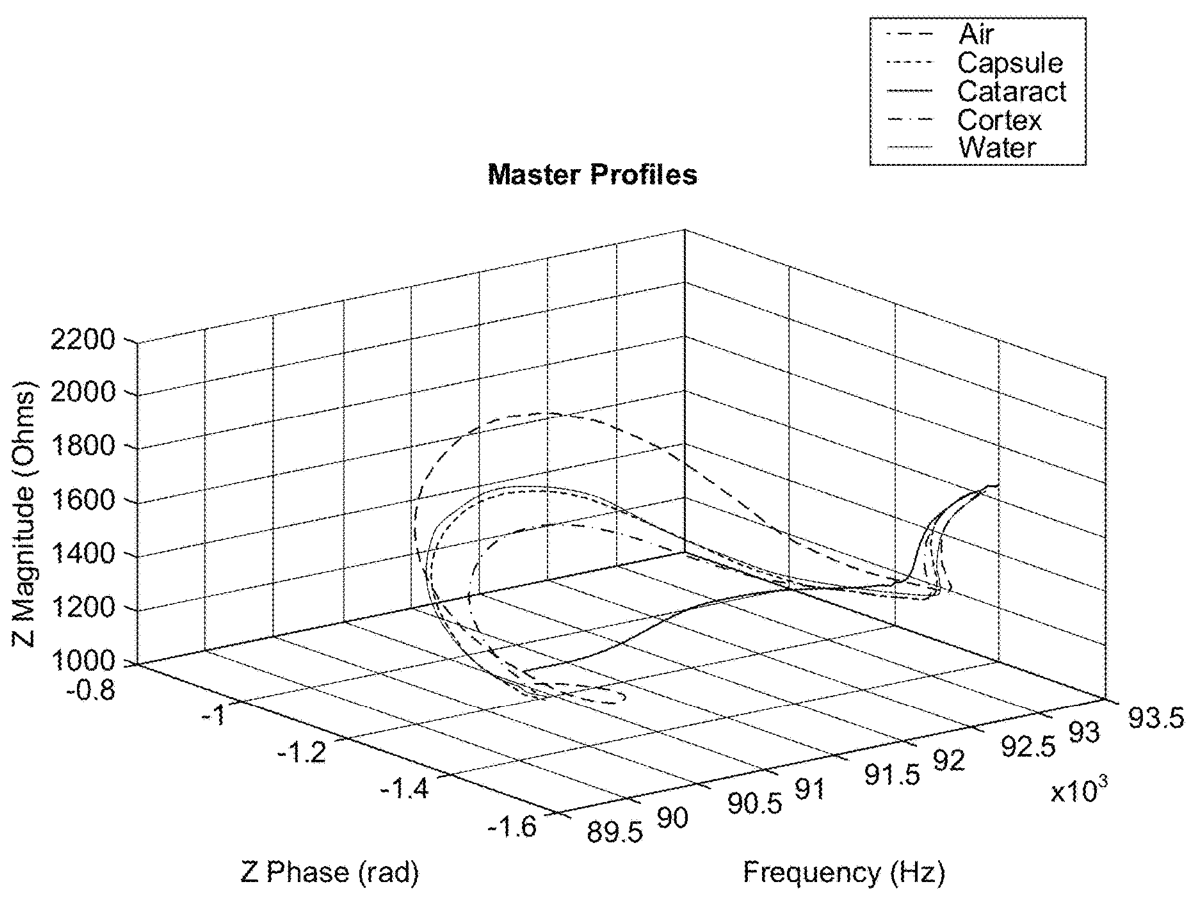
FIG. 10 illustrates an example of a three-dimensional plot of impedance measurement data associated with master profiles for air, lens capsule tissue, cataract tissue, cortex, and water.

FIG. 10 illustrates an example of a three-dimensional plot of impedance measurement data associated with master profiles for air, lens capsule tissue, cataract tissue, cortex, and water. Following the examples shown in FIGS. 7-9, FIG. 10 illustrates measurement data captured for sensing signals that are swept over a frequency band of ranging at least from 89.5 KHz to 93.5 KHz. As shown in FIG. 10, frequency data is plotted along the x-axis, impedance magnitude data is plotted along the y-axis, and impedance phase data is plotted along the z-axis.

Figure 11:
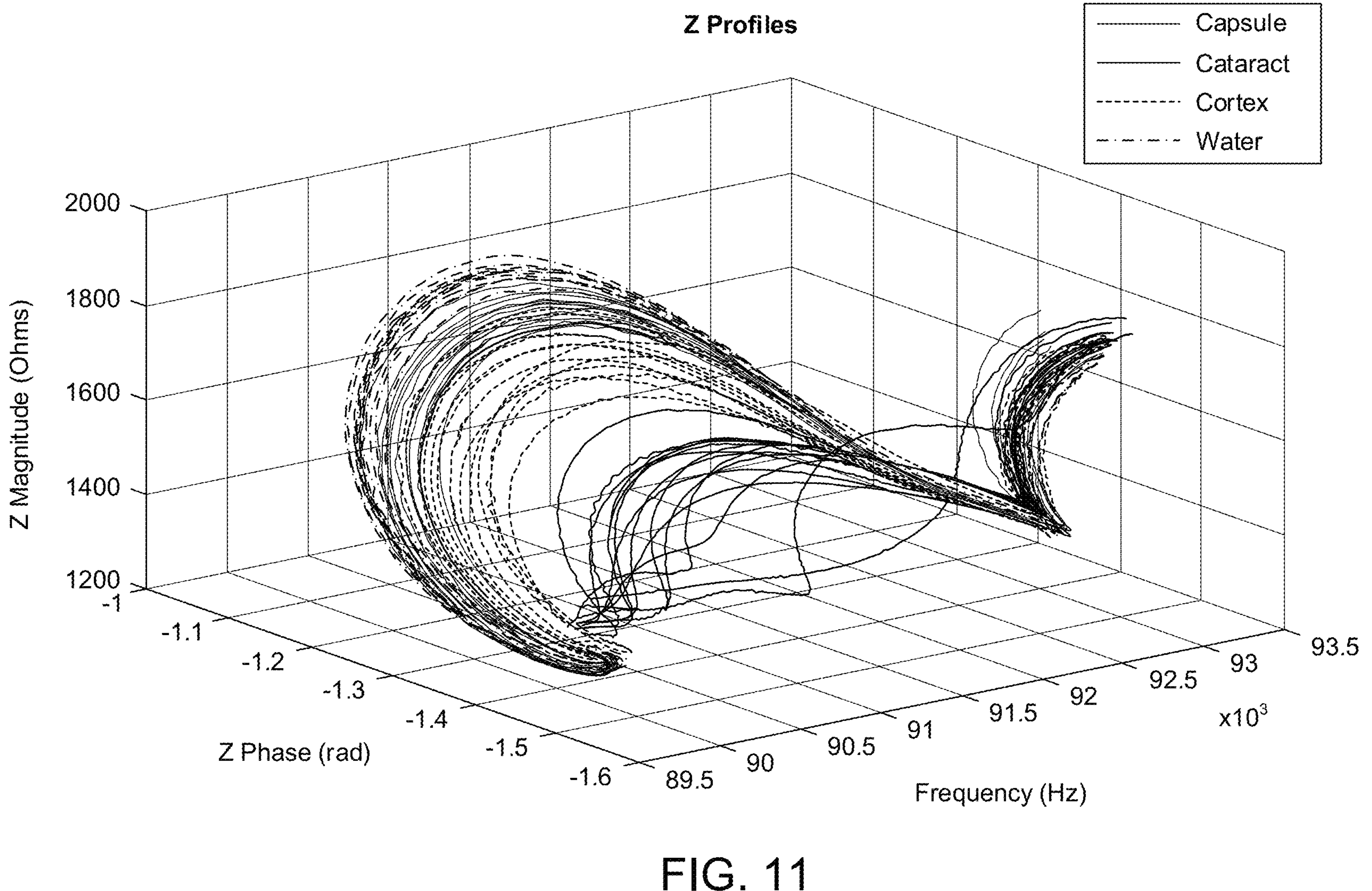
FIG. 11 illustrates a further example of a three-dimensional plot of impedance measurement data captured for air, lens capsule tissue, cataract tissue, cortex, and water.

FIG. 11 illustrates a further example of a three-dimensional plot of impedance measurement data captured for air, lens capsule tissue, cataract tissue, cortex, and water. As shown in the example of FIG. 11, impedance measurement data captured in separate instances for the same medium may exhibit variation between each instance. For example, although impedance measurement data for cataract tissue as shown in FIG. 11 may be readily distinguished from impedance measurement data for lens capsule tissue, cortex, and water, each of the curves representing measurement data captured in a given instance exhibit at least some degree of deviation from each other. The same may be said for measurement data collected for lens capsule tissue, cortex, and water.

To classify the material or medium that the needle is in contact with, the response signal at the needle is measured in real-time and compared with predetermined master impedance profiles. The comparison may involve one or more of a variety of calculations for each of the pre-loaded classes. For instance, the comparison may include the calculation of a deviation value for each of the pre-loaded classes.

One algorithm for calculating deviation values may be an adjusted fuzzy K-means clustering classification algorithm, in which sample impedance profiles of each class from a training dataset are averaged to find their mean impedance phase and impedance magnitude values for each frequency along the frequency sweep. These mean profiles may then be saved as "master" profiles, representing the mean impedance profile for each given material. These master profiles represent the "K-means" of the algorithm, where "K" represents the number of classes. In this example, there may be, for example, five trained classes corresponding to air, capsule, cataract, cortex, and water. In other examples there may be more or less classes (E.g., cataract and non-cataract). To perform the classification on new data (test data), at each frequency value along the frequency sweep, the K-means algorithm calculations are performed, evaluating the Euclidean distance between the given test data point and the pre-trained "master" profile data points.

A three-dimensional Euclidean distance between the curve of the measured response signal and a pre-determined baseline master profile may be determined at each frequency data point, for example, as shown in Equation 1 (Eq. 1) below.

$$P_nP_m = \sqrt{(x_m - x_n)^2 + (y_m - y_n)^2 + (z_m - z_n)^2} \quad \text{Eq. 1}$$

In the deviation calculation of Eq. 1, for a given data point $P_n$ of a master profile, $x_n$ represents a frequency value of the master profile, $y_n$ represents an impedance phase value of the master profile, and $z_n$ represents an impedance magnitude value of the master profile. In addition, for a corresponding data point $P_m$ in a set of captured measurement data, $x_m$ represents a measured frequency value, $y_n$ represents a measured impedance phase value, and $z_m$ represents a measured impedance magnitude value.

The deviation values calculated at each frequency data point may be summed to obtain a single deviation value that represents the total amount of deviation of the measurement data from the master profile. Equation 2 (Eq. 2) illustrates an example of a formula as may be used to sum the deviation values.

$$\sum \begin{bmatrix} \text{Distance @ lower bound of frequency range} \\ \vdots \\ \text{Distance @ upper bound of frequency range} \end{bmatrix} = \text{Total Deviation} \quad \text{Eq. 2}$$

As shown in Eq. 2, the total deviation may be calculated as the sum of the deviation values between the lower bound of the frequency range in which measurement data is captured and the upper bound of the frequency range in which measurement data is captured.

Having calculated the sum of deviation values taken across the frequency values, the medium corresponding to the master profile having the smallest deviation value is predicted as the medium that the needle is in contact with. A confidence level may be calculated for the classification prediction to provide a probability as to whether the classification of the medium is correct. This metric could be used to limit the output effects of the algorithm, such that instead of turning off power to the handpiece it may simply alert the user, via audible, visual, tactile, or some other form of feedback. The level at which the confidence is considered "acceptable" may be variable, and could be controlled by other variables, such as aspiration pressure, amount of cataract already evacuated, or other variables measured by another system or inputted by a user.

In the above-described example, the classification prediction may be similar to a fuzzy K-means clustering analysis, because the confidence level may be calculated in the same manner in which a fuzzy K-means algorithm calculates a membership score. In some models, a membership score may describe the estimated probability that a data point belongs to a given classification. In some models, each data point is a member of all possible classifications and is assigned a membership score for each classification. The sum of all membership scores is equal to 1. In some models, the classification for which a data point has the highest membership score may be considered the classification assigned to the data point.

In some examples, a Gaussian Mixture Model may be used for a similar purpose, such as to provide membership scores. To account for surgeon technique and preference, the membership scores corresponding to each classification may be configurable. For example, the membership scores may be preconfigured, user configurable, or remotely configurable via a network interface. A surgical system may be configured with one or more default values by which the system would classify a sensed medium as cataract tissue in response to computing a membership score of 0.7 or above. In other words, in this example, a computed membership score of 0.7 or above may cause the system to behave as if it were in contact with cataract tissue (e.g., activating ultrasonic power to the handpiece). A surgeon preferring that a higher level of certainty before activating ultrasonic power may choose to adjust this threshold to something higher than 0.7, such as 0.9. This would enable surgeons to customize the threshold membership score at which a classification would be acted upon by the system.

FIG. 12 is a table illustrating an example of deviation data calculated across multiple sets of measurement data. As shown in FIG. 12, each name corresponds to a separate set of measurement data. Although not shown in FIG. 12, deviation data may be calculated across a curve for a range of frequencies at which the measurement data is captured with data points of master profiles of potential media. The deviation data across the calculated range of frequencies may be summed substantially as described in paragraphs above. Summed deviation data may be tabulated for each master profile that the captured measurement data is compared with as shown in FIG. 12. The predicted classification and calculated confidence interval may also be stored for each set of measurement data. Those of ordinary skill in the art will appreciate that the table of FIG. 12 is provided to visually illustrate data as may be stored logically in a database of a computer-implemented system, and tabulation of such data may be performed in a different manner. In some examples, the stored data may include only a subset of the data described with respect to FIG. 12, while in other examples, the data shown in FIG. 12 may be accompanied by other data.

Alternate examples may include any algorithm used for classification or pattern recognition. In some examples, the predicted classification may be determined using an artificial intelligence (AI) application. An algorithm employing a classifier function may be tuned based on data of one or more master profiles and recognize a pattern in impedance measurement data that predicts a given classification. In some examples, due to the nature of the materials being classified, a machine learning classification algorithm may be capable of distinguishing between cataract and non-cataract tissue. A model, such as an artificial neural network (ANN) may be trained using master profile data and/or other previously collected impedance measurement data. The data used as input features to the algorithm (frequency, impedance phase, and impedance magnitude) may be scaled to improve algorithm performance.

Pre-clinical, clinical, and/or simulation data may be used alone or in combination to train the machine learning models responsible for the classification. Pre-clinical data may include data captured during procedures involving porcine, rabbit, or other types of animal eyes. Clinical data may include real-world data captured during procedures involving human patients. Simulation data may include data obtained from deductive models formed from previously collected data (e.g., preclinical and/or clinical data). The simulation data may include predicted impedance measurements (potentially as well as other parameters) for specific surgical scenarios. A model for generating such simulation data may be developed based on patterns observed in pre-clinical and/or clinical data.

An example may include any machine learning classification algorithm in which the data (including, e.g., frequency, impedance phase, impedance magnitude, vacuum pressure, aspiration flow rate) are used as inputs to the model to identify both occlusion status (i.e., whether the system is occluded or not occluded) and material classification. As described above, the machine learning algorithm may be a clustering algorithm (e.g., a fuzzy clustering algorithm) that classifies data points based on similarity. The machine learning algorithm may be a distribution-based clustering algorithm. Other examples of algorithm types that may be used to classify impedance measurement data include density-based clustering, grid-based clustering, hierarchical clustering, and centroid-based clustering. In some examples an algorithm may employ a combination of the above-reference classification methods. Specific examples of applicable types of machine learning models include but are not limited to: Support Vector Machines (SVM), Random Forests, K-Nearest Neighbors, Logistic Regression. In particular, an SVM algorithm may be useful for this application due to the need for rapid, real-time classification. Once trained, an SVM model may have low computational power requirements for subsequent computations, making it particularly useful for the present application.

Figure 14:
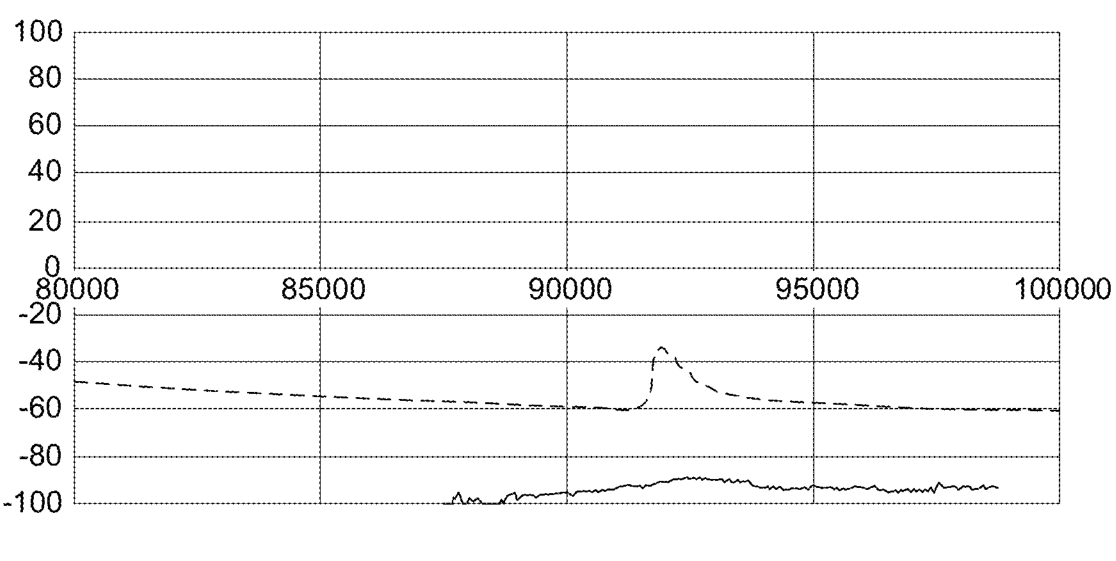
Figure 16:
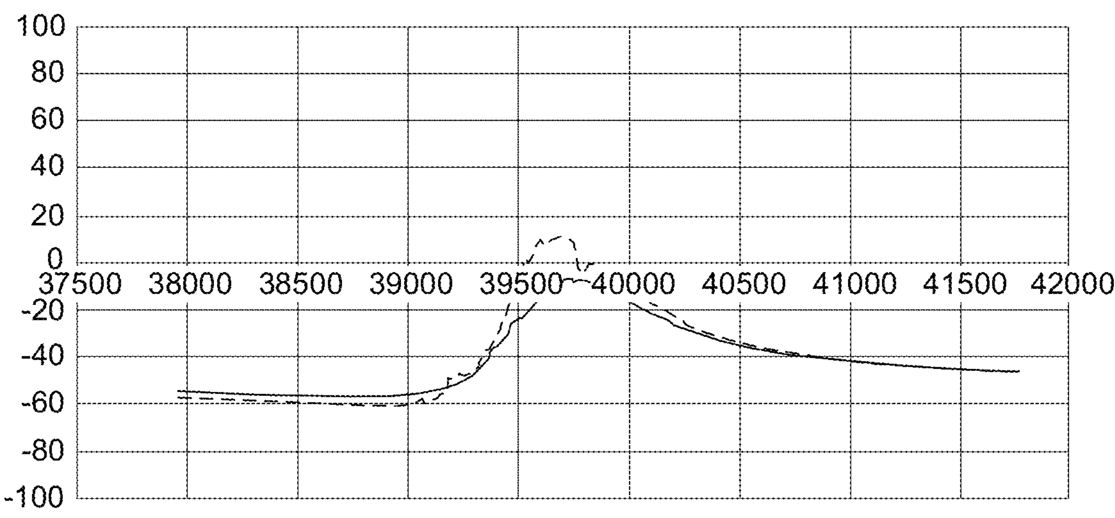
Figure 17:
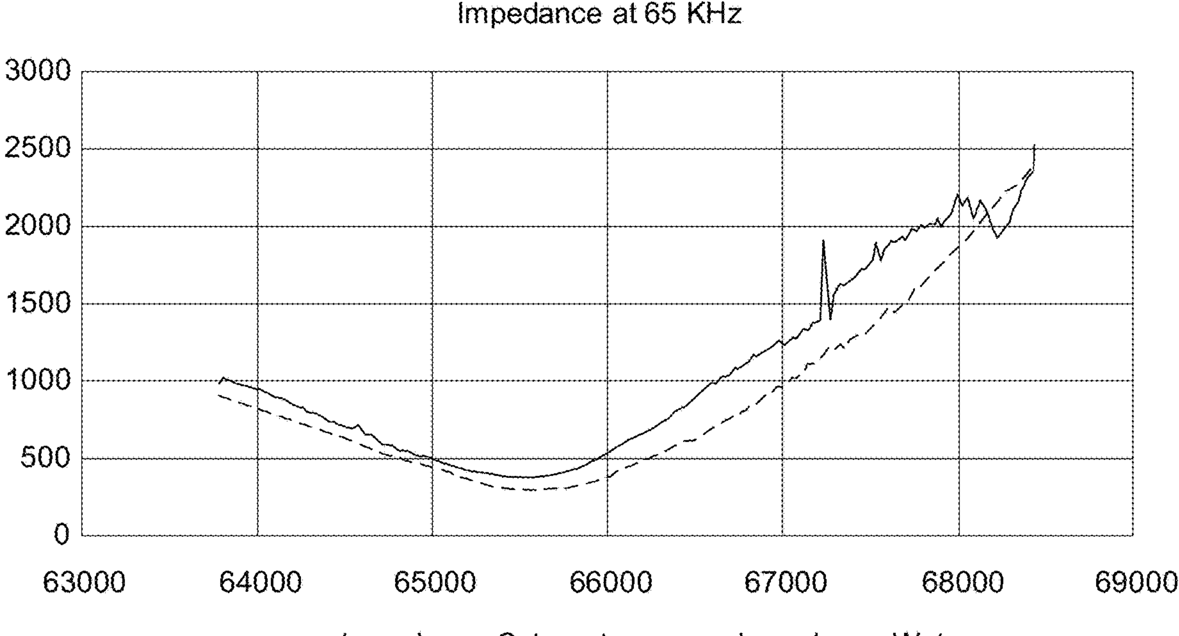
FIGS. 17 and 18 respectively illustrate impedance magnitude and impedance phase data measured within a frequency band centered around 65 KHz.
Figure 18:
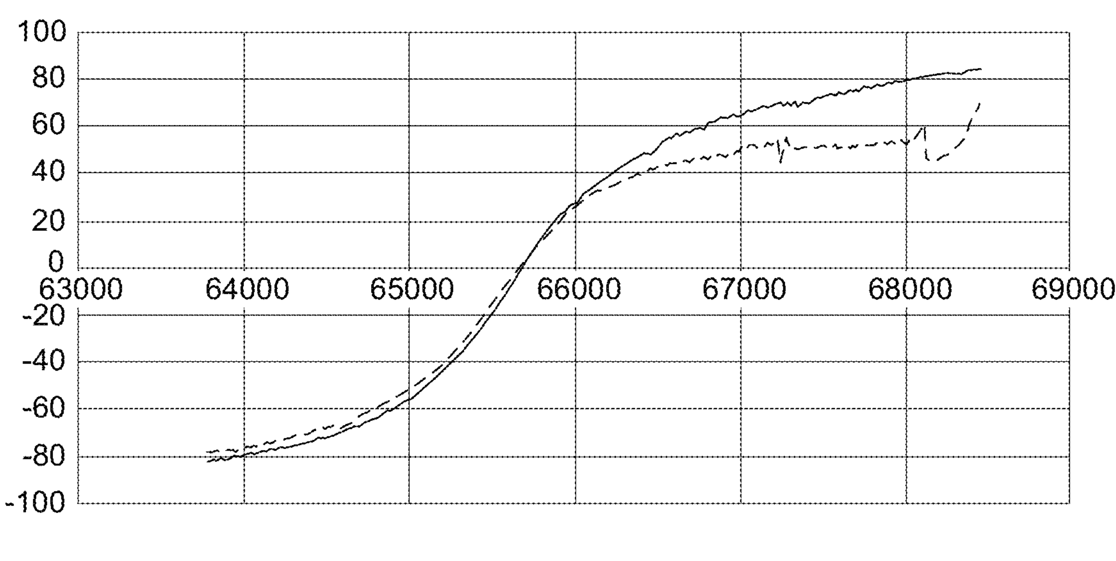
Figure 19:
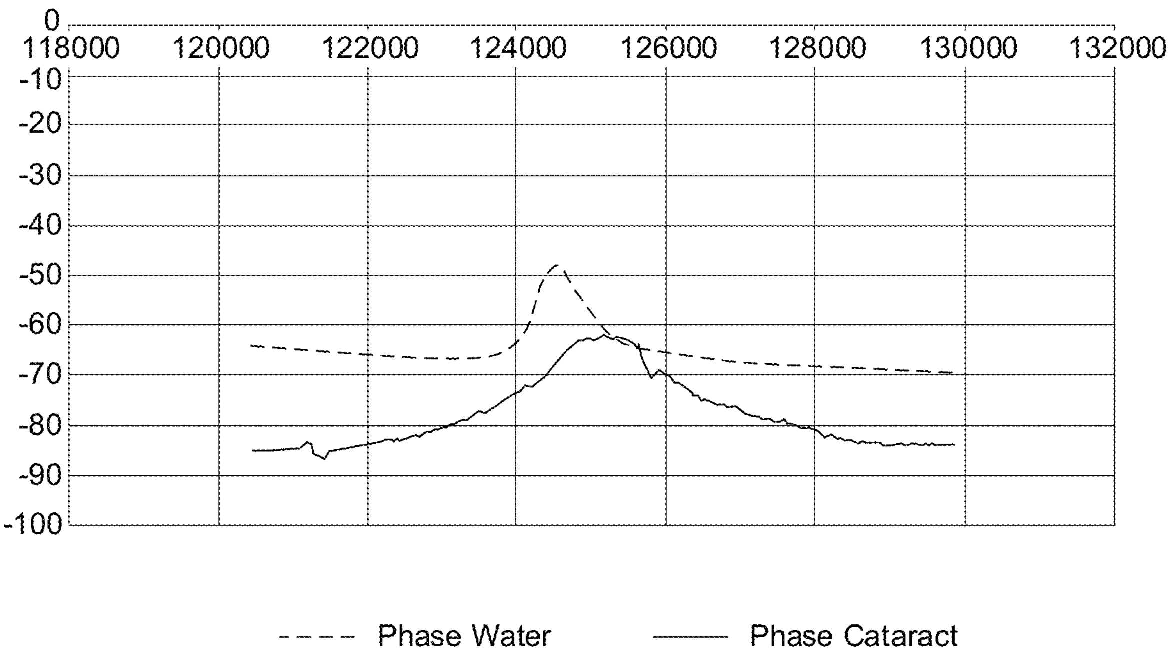
FIGS. 19 and 20 respectively illustrate impedance magnitude and impedance phase measured within a frequency band centered around 125 KHz.
Figure 20:
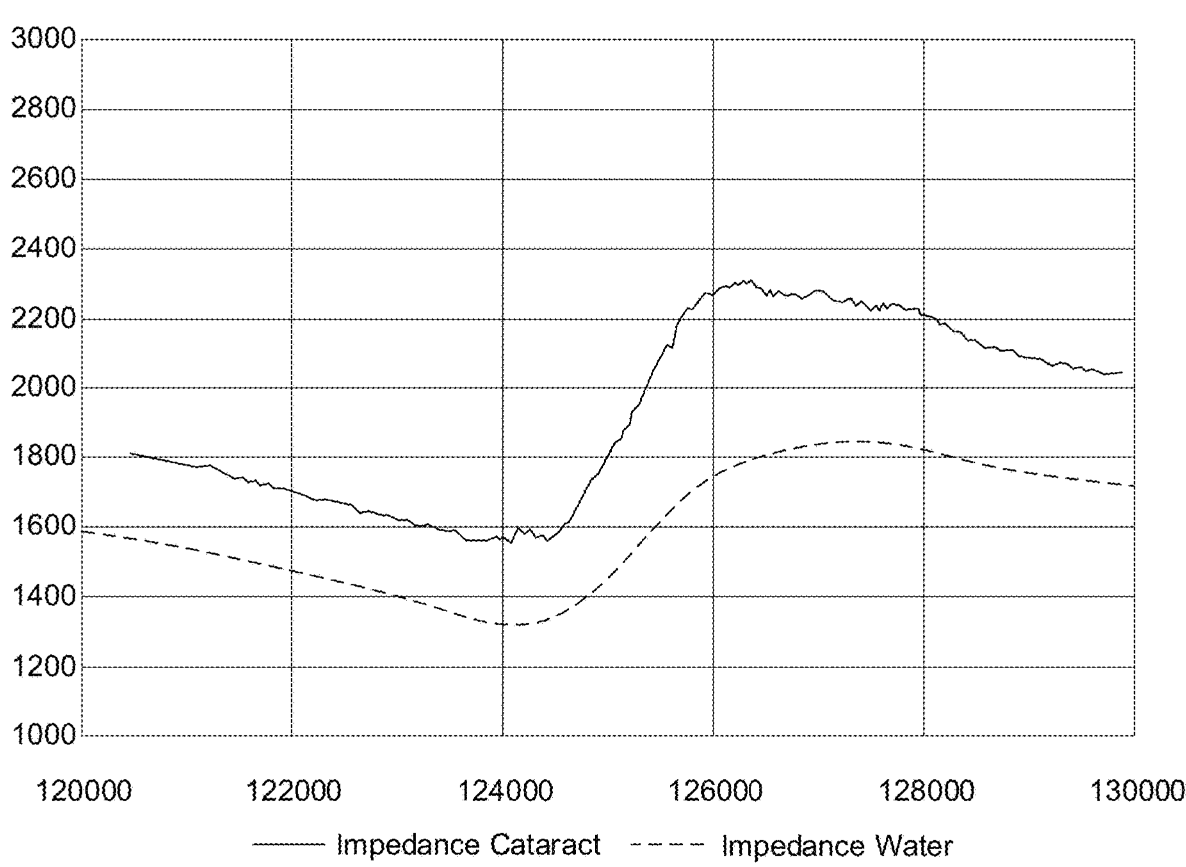

FIGS. 13-20 illustrate comparisons of impedance profile data captured at various frequencies when an ultrasonic handpiece is in contact with a cataract and in contact with water. FIGS. 13 and 14 respectively illustrate impedance magnitude and impedance phase data measured within a 91 KHz band. FIGS. 15 and 16 respectively illustrate impedance magnitude and impedance phase data measured within a 39 KHz band. FIGS. 17 and 18 respectively illustrate impedance magnitude and impedance phase data measured within a 65 KHz band. FIGS. 19 and 20 respectively illustrate impedance magnitude and impedance phase measured within a 125 KHz band.

In some examples, impedance measurement data may vary based on the configuration or characteristics of the ultrasonic handpiece. For instance, one or more of the frequency, impedance magnitude, and/or impedance phase data captured for the same medium may differ depending on at least one or more of the type(s) of ultrasonic handpiece used or the components of the ultrasonic handpiece. The tip of the ultrasonic handpiece includes a needle having a distal tip (referred to interchangeably herein as a "distal end") through which fluid and emulsified portions of the cataract are aspirated. The shape and size of the needle used in a particular procedure may depend on the surgeon's preferences and circumstances specific to a given patient's procedure. The needle used in a particular procedure may be selected for greater efficacy in certain aspects such as chopping or shaping of the hardened cataract. For example, the needle may be bent, straight, or flared. The tip of the needle may be beveled (e.g., at 30 degrees or 45 degrees) or reverse beveled. The needle may be available in a variety of different sizes. For example, a 20 gauge needle may have a tip with an outer diameter of 0.8 mm or 0.031 inches. A 21 gauge needle may have a tip with an outer diameter of 0.9 mm or 0.035 inches. The needle used in a procedure may also be selected based on whether the surgeon prefers higher (i.e., faster) or lower (i.e., slower) flow. A higher gauge (e.g., 21 gauge) needle will provide a lower flow, while a lower gauge needle (e.g., 19 gauge) will provide a higher flow. The algorithm used for classification may account for one or more of such properties of the needle, such that the differences in the electro-mechanical behavior of the system when different needle are used are accounted for. This may ensure that the classification is being made based on the material in contact with the tip of the device and is not being skewed by the electro-mechanical properties of the device itself.

Figure 21:
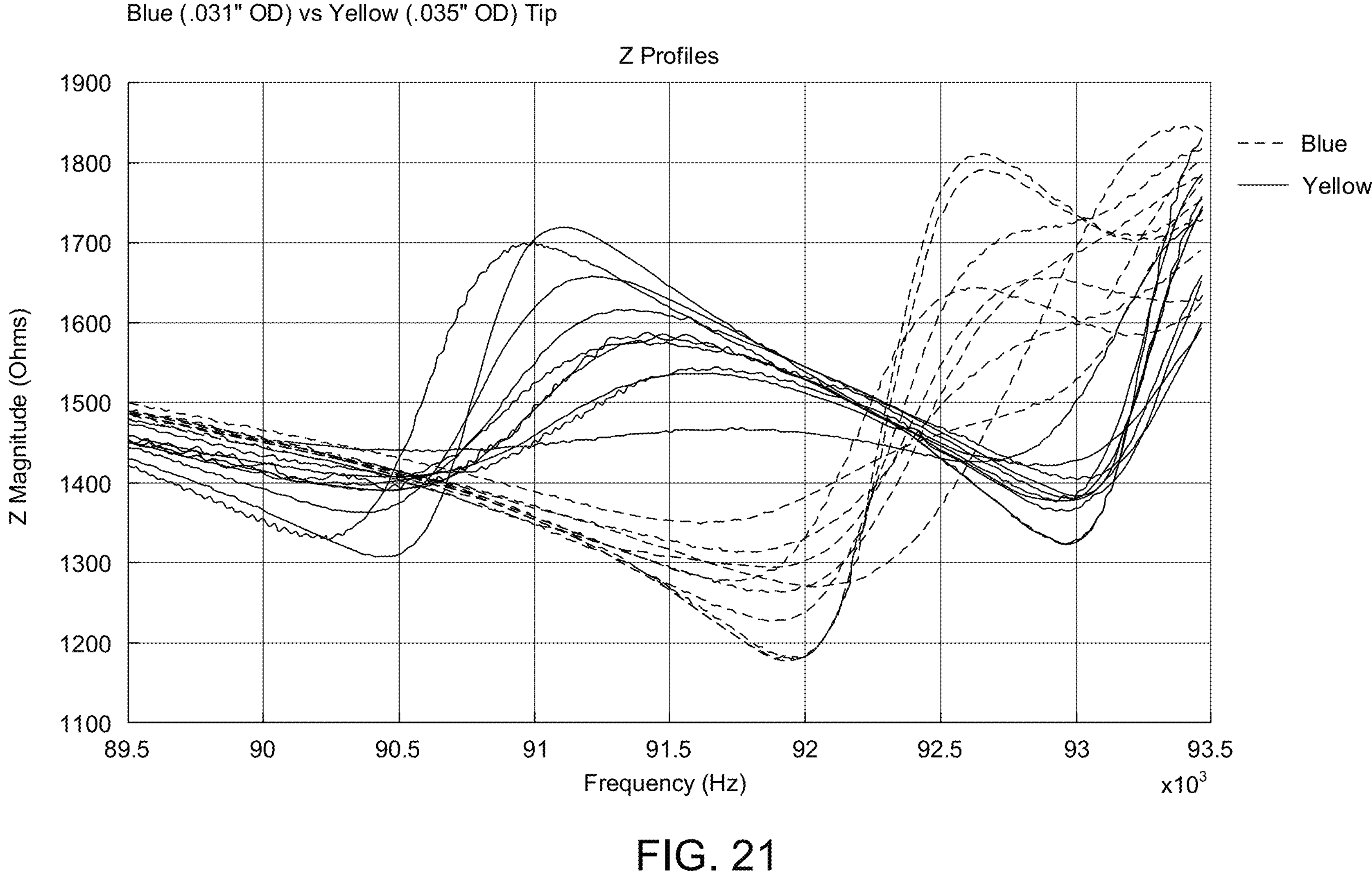
FIG. 21 illustrates a comparison of impedance measurement data captured for needle having different outer diameters.

FIG. 21 illustrates a comparison of impedance measurement data captured for needle having different outer diameters. Specifically, several impedance profiles are shown for each of measurement data captured for a needle with a tip having a 0.031 inch outer diameter and impedance measurement data captured for a needle with a tip having a 0.035 inch outer diameter. As shown in FIG. 21, the profiles for the 0.031 inch outer diameter tip exhibit impedance characteristics that are distinct from the profiles for the 0.035 inch outer diameter tip.

Systems and methods for sensing media during a phacoemulsification procedure are described in the following paragraphs. Systems and methods as described herein may be used for example, during a surgical procedure or in calibrating a sensing system as may be later used during the surgical procedure. More specifically, systems and methods proposed herein are provided both for generating impedance profiles and for the sensing that is carried out during a surgical procedure by way of comparison between impedance measurements and stored impedance profiles.

Figure 22:
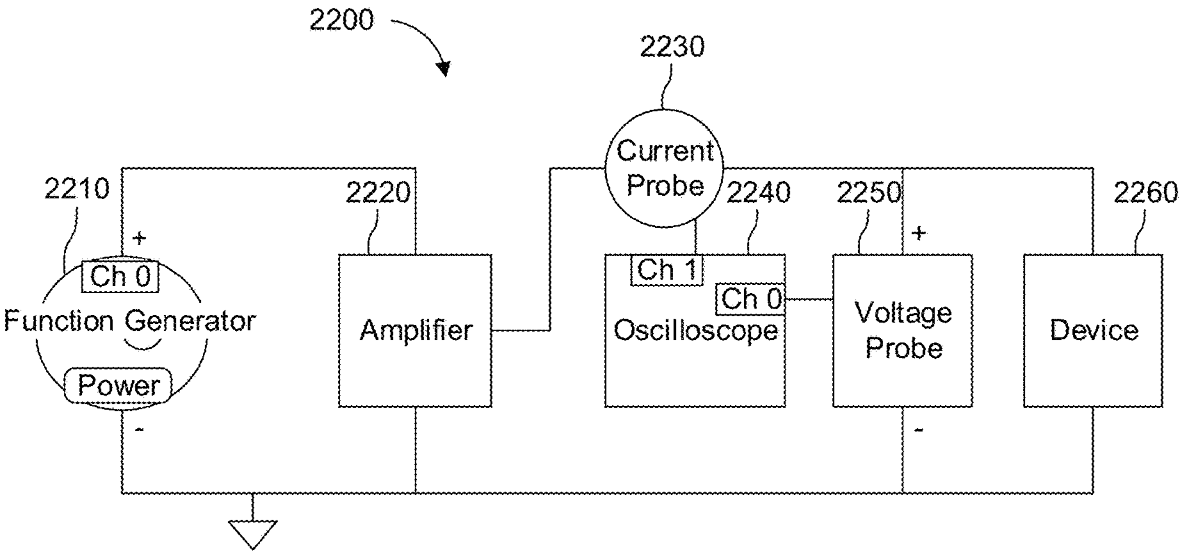
FIG. 22 is a system diagram illustrating an exemplary system through which one or more methods described herein may be implemented.

FIG. 22 is a system diagram illustrating an exemplary system through which one or more methods described herein may be implemented. Although a specific assignment of functionality to system elements is described, those of skill in the art will understand that any technically feasible assignment of functionality to system elements is within the scope of the present disclosure.

As shown in FIG. 22, the system 2200 may include a function generator 2210, an amplifier 2220, a current probe 2230, an oscilloscope 2240, a voltage probe 2250, and a device 2260. The device 2260 may be, for example, an ultrasonic handpiece, such as a VERITAS™ Swivel handpiece, an ELLIPS™ FX handpiece, or a WHITESTAR™ Phaco handpiece. In other examples, the device may be a subsystem or component of an ultrasonic phacoemulsification system that utilizes an ultrasonic handpiece, an interface coupled to an ultrasonic handpiece, or a processing device coupled to or implemented in the ultrasonic handpiece.

The function generator 2210 is configured to produce an arbitrary waveform, i.e., a signal swept across a predefined frequency range. For example, the function generator 2210 may be user configurable (e.g., via a user interface) to drive and/or read signals at various frequency ranges. The amplifier 2220 is coupled to the function generator 2210 and is configured to operate at a low power for safety and to prevent damage to the equipment, while still driving the produced waveform at a sufficient power to maintain a steady signal.

The current probe 2230 and the voltage probe 2250 are coupled with the amplifier and with the device 2260 to measure a current and voltage of the sinusoidal waveform. An oscilloscope 2240 is coupled with both the current probe 2230 and the voltage probe 2250 over different channels, enabling measurement and analysis of the signal delivered at the device 2260.

In some examples not shown, the system 2200 may include a console (e.g., a phacoemulsification console). The console may include one or more processing devices or processors (i.e., integrated circuit, field programmable gate arrays (FPGAs)) and memory devices (i.e., non-volatile memory, read-only memory, read/write memory, etc.). The console may be connected with one or more of the device 2260, function generator 2210, the amplifier 2220, the current probe 2230, the oscilloscope 2240, and/or the voltage probe 2250. In some examples, one or more of the device 2260, function generator 2210, the amplifier 2220, the current probe 2230, the oscilloscope 2240, and/or the voltage probe 2250 may be implemented in the console as an integrated system via the processor(s) and one or more sensors. Though not portrayed, the console may further include a foot pedal that is coupled with the device 2260 and configured to accept an input from a user as well as an audio/visual display device (e.g., a GUI) configured to display data, recommendations, and issue warnings from the system to the user. The console may be configured with software or firmware which, when executed by a processor, causes the console to perform one or more steps described herein.

In some examples not shown, the console may include circuitry, pumps, valves, sensors, and/or other hardware for controlling an ultrasonic handpiece, fluidics subsystem, and related surgical parameters. For example, the console may include a fluidics controller that has one or more processing devices or processors (i.e., integrated circuits, FPGAs) and memory devices (i.e., non-volatile memory, read-only memory, read/write memory, etc.). The fluidics controller may be configured with software or firmware which, when executed by a processor, causes the console to perform one or more steps described herein. In some examples, the console may include an ultrasonic subsystem controller that is configured to control the activation/deactivation of ultrasonic power.

Alternate examples of the hardware used in the system may include any system capable of delivering a signal across a spectrum sweep of frequencies and measuring the impedance magnitude and phase of the ultrasonic hand-piece frequencies within the spectrum.

In some examples, a system may have the ability to simultaneously send the subtherapeutic, low power, sensing signal and the normal ultrasonic energy signal that is actually driving the motion of the tip. This may enable the device to keep sensing while the device is actively emulsifying the cataract. In some examples, the system may rapidly alternate between sending the sensing signal and activating the ultrasonic power.

Figure 23:
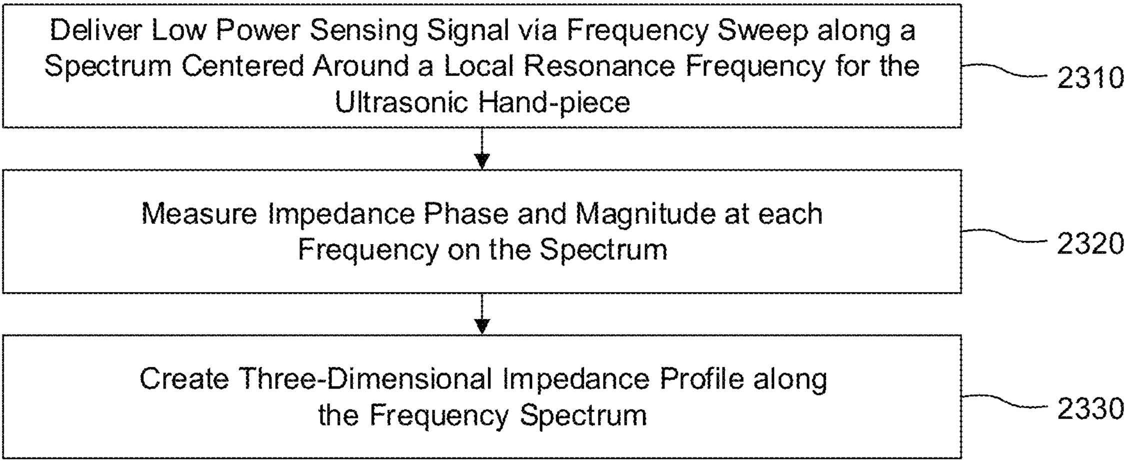
FIG. 23 is a flowchart illustrating an example of a method for measuring impedance characteristics of material in contact with the needle of the ultrasonic handpiece and classifying the material.

FIG. 23 is a flowchart illustrating an example of a method for measuring impedance characteristics of material in contact with the needle. As shown at 2310, an implementing system generates or delivers a sensing signal to the needle. The signal is swept over a frequency spectrum centered at a local resonance frequency for the ultrasonic handpiece. The needle may contact the medium to be classified e.g., before the sensing signal is delivered, or while the sensing signal is delivered. At 2320, the system measures an impedance phase and magnitude of the sensing signal at each frequency on the spectrum. At 2330, based on the measured impedance phase and magnitude at each frequency, the system stores the impedance measurement data. In doing so, the system may create a three-dimensional impedance profile along the frequency spectrum.

Figure 24:
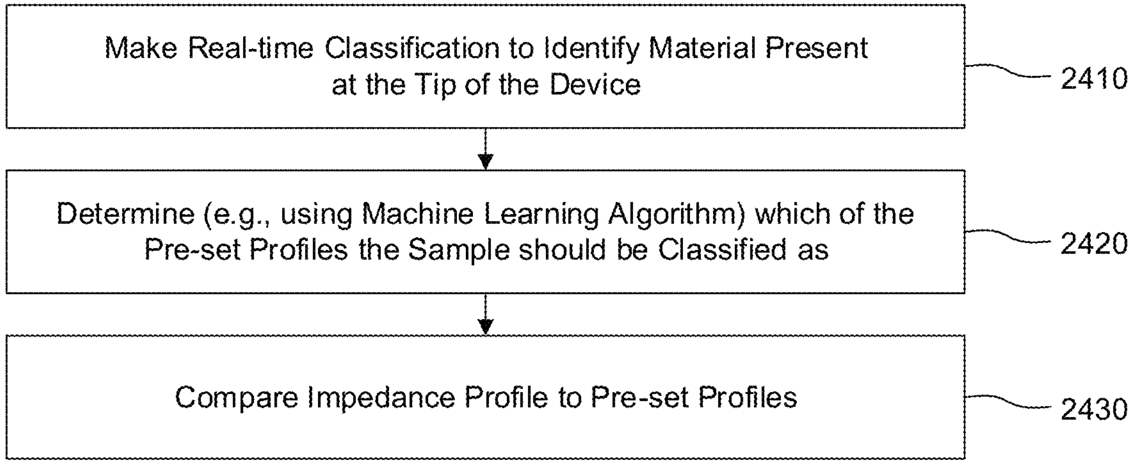
FIG. 24 is a flowchart illustrating an example of a method for classifying the output of an ultrasonic handpiece.

FIG. 24 is a flowchart illustrating an example of a method for classifying the output of an ultrasonic handpiece. As shown at 2410 an implementing system compares impedance measurement data (e.g., in the form of the stored three-dimensional impedance profile) with pre-set impedance profiles for various media. At 2420, the implementing system makes a real-time classification as to the material/medium present at the tip of the device. The classification is based at least on the comparison between the impedance measurement data and the pre-set impedance profile and may be carried out according to one or more of the methods described above. For example, the comparison may involve calculating and summing deviation data between measurement data and the pre-set profiles. In some examples, the classification may be made by using artificial intelligence (e.g., a machine learning algorithm). Other data or a combination of other data could be used in the classification algorithm, including vacuum pressure, aspiration flow rate, etc. Some algorithms may incorporate other data into the model, such as the tip diameter of the phacoemulsification device, the tip type, and any other factors than may influence the impedance of the ultrasonic handpiece.

Figure 25:
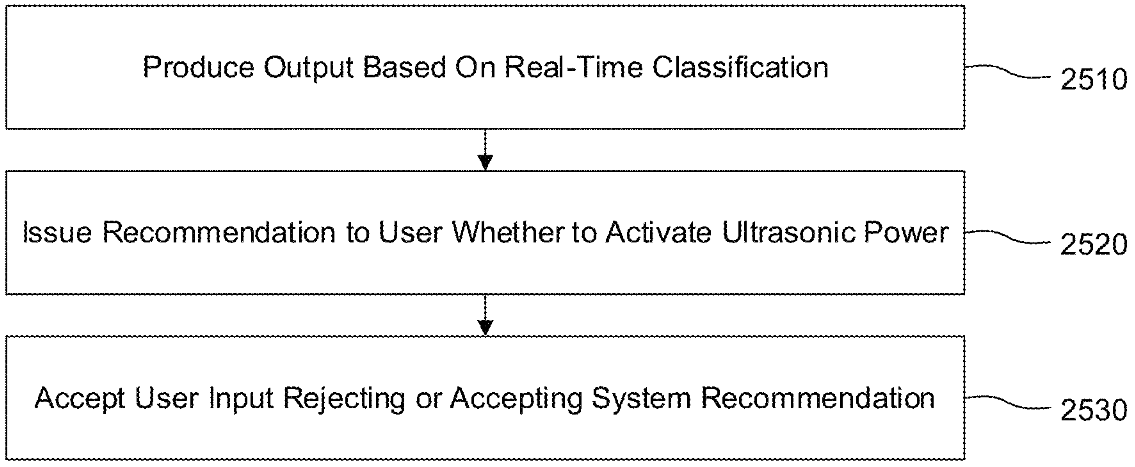
FIG. 25 is a flowchart illustrating an example of a method for controlling an output of an ultrasonic handpiece.

FIG. 25 is a flowchart illustrating an example of a method for controlling an output of an ultrasonic handpiece. As shown at 2510, the implementing system produces an output based on the real-time classification that is in turn made based on the impedance measurement data. At 2520, the system responds to the output, such as by allowing ultrasonic power to be delivered, or by preventing ultrasonic power from being delivered. In some examples, the output may be interpreted as a recommendation from the system to deliver or prevent delivery of ultrasonic power. Accordingly, the system may indicate the recommendation to the user. As shown at 2530, a user (e.g., the surgeon, nurse, or other operating room staff) may override the response or recommendation of the system, if desired. For instance, the system may be configured to accept an input from a user rejecting the response or recommendation, substantially as described in paragraphs following herein.

The tissue sensing feature may be enabled or disabled according to the preferences of the user. Such preferences may be configured as program settings during system setup prior to or during a surgical procedure. For instance, tissue sensing may be configurable for individual phacoemulsification sub-modes or enabled/disabled by default for all modes. Various methods of inputting settings relating to tissue sensing may be used, such as entry via a graphical user interface provided by a console or another component of the surgical system. Another method may include entry by a user of a computer application (e.g., a web-based or mobile application). Yet another method may provide for automatic configuration of tissue sensing parameters based on other configured system parameters such as: an active phacoemulsification mode or sub-mode, fluidics parameters in use by the surgical system, the surgical equipment in use such as a handpiece type, a tip/needle type, a foot pedal type, and/or power settings for the surgical system.

As described in paragraphs above, the tissue sensing feature may be deployed in a system in which a surgeon manually controls fluidics and ultrasonic parameters during the procedure. For example, the tissue sensing feature may be implemented in a system in which a control device (such as a foot pedal) is used to switch between various "modes." A foot pedal in some examples may be operable by pressing (or depressing) a treadle that rotates axially about a hinge. The foot pedal may be rotated through a range of motion divided into multiple "zones." The foot pedal may be spring actuated such that the treadle returns to a resting position when released by the surgeon.

For example, a foot pedal may be configured to rest at a starting position referred to as foot pedal zone 0 (FP0). When the pedal rests at its starting position (i.e., FP0), the surgical system is in an idle state such that there is no irrigation, aspiration, or ultrasound activated and the system is awaiting user control via movement of the foot pedal into FP1, FP2, or FP3. When the foot pedal is pressed, its initial range of motion may be referred to as foot pedal zone 1 (FP1). Pressing the foot pedal within FP1 may cause the surgical system to control irrigation flow from the surgical console, through the ultrasonic handpiece and to the patient's eye. Further actuation of the foot pedal into foot pedal zone 2 (FP2) may cause the surgical system to activate and control simultaneous irrigation and aspiration flow. Finally, further actuation of the foot pedal into foot pedal zone 3 (FP3) may cause the surgical system to activate and control ultrasonic power simultaneously with irrigation and aspiration flow.

In some examples, when enabled, the tissue sensing feature may be active when a surgeon presses a foot pedal to move the pedal into FP2 and remain active as the surgeon presses the foot pedal to move into FP3. As the surgeon presses on the foot pedal and moves into FP3 to apply ultrasound power, the tissue sensing feature may be active and continuously classify the material in contact with the needle to ensure that power is being applied accordingly and appropriately for the cataract material (i.e., as opposed to other tissue not to be removed and/or emulsified). If the engaged material is profiled as cataract material, power may be delivered to the handpiece in the percentage/level the user had initially programmed into program settings at the start of the surgical procedure (e.g., as long as the foot pedal remains within FP3). If the engaged material is profiled as non-cataract tissue, power delivery to the handpiece may be halted if the foot pedal has already been moved into FP3. A visual indication on the system display, or an auditory indication from the system, may provide insight to the user that the tissue sensed is profiled as non-cataract.

In another scenario, if the surgeon has pressed the foot pedal to move into FP3 and the needle contacts non-cataract tissue, the surgical system may be configured to halt ultrasonic power. If, while the needle is in contact with non-cataract tissue and the surgeon releases or controls the pedal to move back to FP0 before immediately moving back into FP3, the surgical system may continue to prevent ultrasonic power from being activated. A similar situation may arise, for example, when a surgeon "feathers" the foot pedal by maintaining the position of the foot pedal at a position that borders two zones (e.g., FP2 and FP3), potentially while moving rapidly back and forth between zones via a small range of motion. The surgical system may be configured to detect that the surgeon is feathering the foot pedal based on various characteristics such as the amount of time spent in a given foot pedal zone, based on an amount of force applied to the treadle by the surgeon, based on the speed at which the foot pedal travels, or based on a level of acceleration of the treadle.

If the user desires to override the tissue sensing algorithm and keep applying power to the tissue currently engaged at the time despite being classified as non-cataract, the tissue sensing feature may allow for overriding of the system response. The user may confirm the override of the system response by, e.g., activating a switch on the foot pedal (yaw movement of the pedal left or right) while still maintaining the position of the foot pedal within FP3 to maintain ultrasonic power despite the tissue sensing algorithm identifying non-cataract tissue.

In some examples, the user may maintain/hold the pedal's position within FP3 for a given time interval (e.g., 3 seconds) after the non-cataract tissue is identified and indicated to the user (i.e., via auditory or visual means). This may indicate to the system that the user desires to maintain ultrasonic power despite the characterization of material indicating non-cataract tissue. By allowing the user to maintain the pedal position within FP3 for the time interval before activating ultrasonic power again (as opposed to requiring the user to activate a switch, for example), this may help alleviate potential delays or disruptions in the surgical flow and allow re-activation of ultrasonic power almost immediately. Ultimately, the system and algorithm may support the user and mitigate the risks of applying ultrasonic power to non-cataract tissues or structures in the eye. If the user acknowledges a response/warning issued by the system and yet still decides to override the system recommendations, the goal may be to provide the surgeon what is needed (i.e., power) when desired and as seamlessly as possible.

Figure 26:
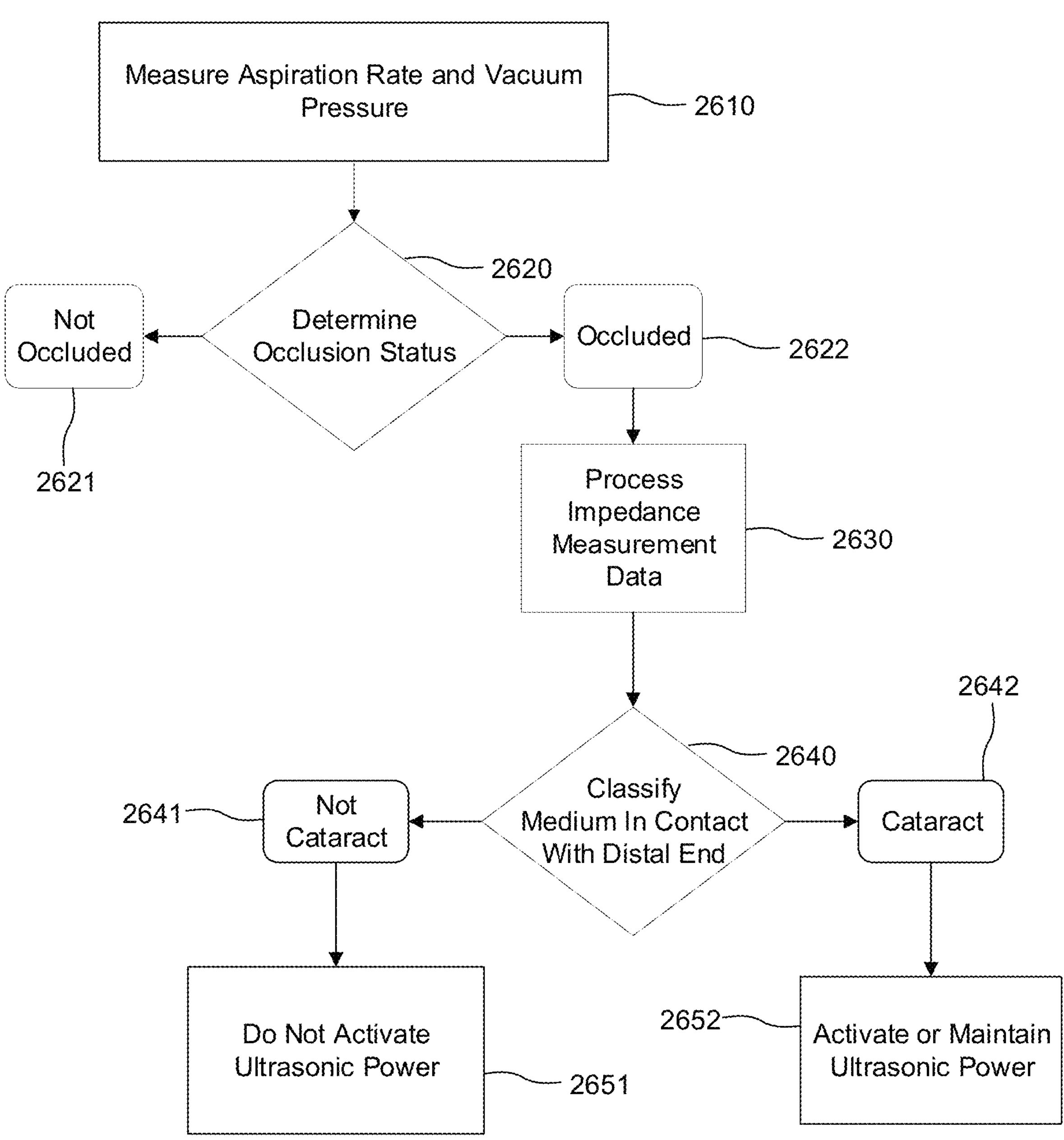
FIG. 26 is a flowchart illustrating an example of a method for measurement and classification of a medium during a surgical procedure.

FIG. 26 is a flowchart illustrating an example of a method for measurement and classification of a medium during a surgical procedure. The method is carried out by a phacoemulsification system including an ultrasonic handpiece with a distal end that comes into contact with tissues of a patient's eye. As shown in FIG. 26, at 2610, a surgical system measures one or more surgical parameters such as aspiration rate and vacuum pressure during the procedure. The surgical system, via a fluidics controller (or a logically equivalent component of the system architecture), may monitor aspiration rate and vacuum pressure and forward the measured surgical parameter values to other physical hardware (e.g., an ultrasonic controller) or virtualized entities (e.g., a host, GUI, or an OS) of the surgical system. The fluidics controller captures the surgical parameter values and forwards these to other portions of the system at regular intervals (e.g., 10 ms).

As shown at 2620, the surgical system is configured to determine whether an occlusion is present at the distal end of an ultrasonic handpiece or within other portions of the fluidics system. The surgical system may determine whether an occlusion is present based on, or in response to, observed surgical parameters or changes in such surgical parameters. For example, an increase in vacuum pressure and a decrease in aspiration rate may be one set of conditions indicating the presence of an occlusion.

If an occlusion is present, as shown at 2622, the system may process (as shown at 2630) impedance measurement data, for example, in accordance with one or more classification techniques (e.g., AI/ML algorithms) described in paragraphs above. The impedance measurement data may include impedance measurements that are captured (e.g., in real time) according to one or more of techniques described in paragraphs above. At 2640, the surgical system classifies the medium that is contacting the distal end. If, as shown at 2641, the surgical system classifies the medium as a material other than cataract or lens tissue/material, the surgical system may refrain from activating ultrasonic power, as shown at 2651. Otherwise, as shown at 2642, if the classified medium is cataract or lens tissue/material, the surgical system may be configured to activate or ultrasonic power to aid in emulsifying the cataract/lens tissue/material and clearing the occlusion, shown at 2652.

The time required for the system to classify the medium as cataract, lens tissue/material, or another material based on the measured impedance values and then take action is dependent on several factors including the capabilities of the processor performing the operation and the ML algorithm used to perform the classification. For example, substantially as described in paragraphs above, some types of algorithms such as the Support Vector Machine algorithm may be attractive due to their time efficiency when making classifications, especially in comparison to other algorithms such as the Fuzzy K-means algorithm. The amount of time required for the ML algorithm to perform the classification may be dependent on, for example, the number of classes (i.e., tissue types) that are to be evaluated. For example, evaluating the impedance measurements against a great number of classes may be a processing-intensive task that requires more time than is needed to evaluate impedance measurements against a fewer number of classes.

In some examples, as shown at 2621, if an occlusion is not present, the system may be configured to not carry out the processing and classification of impedance measurement data. In some examples, the system may continuously measure, sample, and/or store impedance data of signals observed at the distal end of the handpiece. In some examples not shown, the system may continuously classify impedance data regardless of whether an occlusion is present or determined to be present. In some examples, the system may measure, sample, and/or store impedance data and classify a medium in contact with the distal end of the handpiece without activating or deactivating ultrasonic power. In some examples, the system may determine whether to measure, sample, and/or store impedance data based on whether tissue sensing is enabled or activated, for example, according to one or more methods described above.

Delay may be introduced into the above-described operational flow of the system in various ways. For example, the fluidics controller, and/or the other portions of the system may be configured to process the surgical parameter values before executing further steps. The surgical system may need to average a given number of previously captured measurements before the GUI visually displays aspiration rate and vacuum pressure information to the user.

Another design aspect that may potentially introduce delay into the system is the presence or absence of direct lines of communication between hardware and/or virtualized components of the surgical system. For example, if the fluidics controller has a direct communication line to the ultrasonic controller, the fluidics controller may directly convey that a partial or full occlusion is present based on the amount of vacuum built up in the aspiration line and based on the tissue classification. The ultrasonic controller may immediately activate ultrasonic power to attempt to emulsify the occlusion. On the other hand, if the fluidics controller does not have a direct communication line to the ultrasonic controller, then another system component (such as the host or GUI) may need to act as a middleman and communicate with the ultrasonic controller before ultrasonic power can be activated.

In some examples, the tissue sensing feature may be configured with a sensitivity factor that affects the behavior of the classification algorithm(s) during tissue profiling. For example, the sensitivity factor may be adjusted to provide for a more conservative classification that is more likely to classify material as non-cataract and issue a recommendation or command to halt (or avoid initiating) ultrasonic power delivery. For instance, a surgeon may configure the classification algorithms to require that a data point have a membership score above a threshold before assigning the data point a classification. The threshold may be adjustable by the user or automatically by the surgical system. This is another level of customization that may accommodate varying surgical techniques and preferences while still providing the underlying benefit of safety during the surgical procedure. The sensitivity factor may be configured by the user via a user interface (e.g., via a slider displayed on a graphical user interface on the console).

The present application includes at least the following examples:

Example 1

A system (410) for use in a phacoemulsification procedure comprising: a console (428) comprising a processor (438) and a memory device (435); and an ultrasonic handpiece (412) comprising a needle (416) coupled with a distal end of the ultrasonic handpiece (412), wherein the needle (416) comprises a distal end, and wherein, the ultrasonic handpiece (412) is coupled with the console (428); the processor (438) configured to generate a sensing signal through a frequency range centered at a local resonant frequency of the ultrasonic handpiece (412); the processor (438) configured to measure impedance characteristics of the signal at the distal end of the needle (416); the processor (438) configured to compare the measured impedance characteristics of the generated sensing signal with one or more impedance profiles stored in the memory device (435); the processor (438) and the memory device (435) configured to classify, based on the comparison between the measured impedance characteristics and the stored one or more impedance profiles, a medium contacting the distal end of the needle (416); and the processor (438) configured to control an output of the ultrasonic handpiece (412) based on the classification of the medium contacting the distal end of the needle (416).

Example 2

The system of example 1, wherein the measured impedance characteristics comprise impedance magnitude and impedance phase measurements.

Example 3

A system according to examples 1 or 2, wherein the processor is configured to classify the medium contacting the distal end of the needle using a machine learning algorithm.

Example 4

A system of any one of examples 1 to 3, wherein the processor is configured to compare the measured impedance characteristics of the generated sensing signal with one or more impedance profiles stored in the memory device by calculating deviation values at a plurality of frequencies of the frequency range between the measured impedance characteristics and the one or more stored impedance profiles, wherein the processor is configured to calculate a sum, for each stored impedance profile, of the deviation values at the plurality of frequencies, and to classify the medium contacting the distal end of the needle based on the impedance profile corresponding to the lowest calculated sum.

Example 5

A system of any one of examples 1 to 4, wherein the processor is configured to classify the medium contacting the distal end of the needle as one of cataract or non-cataract material.

Example 6

A system of any one of examples 1 to 5, wherein, on a condition the medium contacting the distal end of the needle is classified as non-cataract, the processor is configured to control an output of the ultrasonic handpiece by ceasing delivery of ultrasonic power or by preventing delivery of ultrasonic power.

Example 7

A system of any one of examples 1 to 6, wherein the processor is configured to classify the medium contacting the distal end of the needle based on a diameter or gauge of the distal end of the needle.

Example 8

The system of example 3, wherein the machine learning algorithm uses, to classify the medium contacting the distal end of the needle, one or more of: a Fuzzy K-Means model, a Support Vector Machine (SVM) model, a Random Forest model, a Nearest Neighbors model, or a Logistic Regression model.

Example 9

A system of any one of examples 1 to 8, wherein the console is coupled with a display (436) configured to provide a user interface (440), and wherein the processor is configured to override the output of the ultrasonic handpiece in response to a user input received at the user interface.

Example 10

The system of any one of example 1 to 9, wherein the processor is configured to adjust a sensitivity level to be used in classifying the medium contacting the distal end of the needle in response to a user input received at the user interface.

Example 11

A system of any one of exampled 1 to 10, wherein the processor is configured to determine, based on the classified medium contacting the distal end of the needle, based on aspiration flow data, and based on vacuum pressure data, that an occlusion is present at the distal end of the needle.

Example 12

A method for sensing tissue during a phacoemulsification procedure, the method comprising: generating a sensing signal through a frequency range centered at a local resonant frequency of an ultrasonic handpiece (412); measuring impedance characteristics of the signal at a distal end of a needle (416) coupled with the ultrasonic handpiece (412); comparing the measured impedance characteristics of the generated sensing signal with one or more stored impedance profiles; classifying, based on the comparison between the measured impedance characteristics and the stored one or more impedance profiles, a medium contacting the distal end of the needle (416); and controlling an output of the ultrasonic handpiece (412) based on the classification of the medium contacting the distal end of the needle (416).

Example 13

The method of example 12, wherein the measured impedance characteristics comprise impedance magnitude and impedance phase measurements.

Example 14

A method according to examples 12 or 13, further comprising classifying the medium contacting the distal end of the needle using a machine learning algorithm.

Example 15

A method according to any one of examples 12 to 14, further comprising comparing the impedance characteristics of the generated sensing signal with one or more impedance profiles stored in a memory device by calculating deviation values at a plurality of frequencies of the frequency range between the measured impedance characteristics and the one or more stored impedance profiles; and calculating a sum, for each stored impedance profile, of the deviation values at the plurality of frequencies, and classifying the medium contacting the distal end of the needle based on the impedance profile corresponding to the lowest calculated sum.

Example 16

A method according to any one of examples 12 to 15, further comprising classifying the medium contacting the distal end of the needle as one of cataract or non-cataract material.

Example 17

A method according to any one of examples 12 to 16, wherein, on a condition the medium contacting the distal end of the needle is classified as non-cataract, controlling an output of the ultrasonic handpiece by ceasing delivery of ultrasonic power or by preventing delivery of ultrasonic power.

Example 18

A method according to any one of examples 12 to 17, further comprising classifying the medium contacting the distal end of the needle based on a diameter or gauge of the distal end of the needle.

Examples 19

The method of example 14, wherein the machine learning algorithm uses, to classify the medium contacting the distal end of the needle, one or more of: a Fuzzy K-Means model, a Support Vector Machine (SVM) model, a Random Forest model, a Nearest Neighbors model, or a Logistic Regression model.

Example 20

A method according to any one of examples 12 to 19, further comprising overriding the output of the ultrasonic handpiece in response to a user input received at a user interface.

Example 21

The method of examples 12 to 20, further comprising adjusting a sensitivity level to be used in classifying the medium contacting the distal tip of the needle in response to a user input received at the user interface.

Example 22

A method according to any one of examples 12 to 21, further comprising determining, based on the classified medium contacting the distal end of the needle, based on aspiration flow data, and based on vacuum pressure data, that an occlusion is present at the distal end of the needle.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A system for use in a phacoemulsification procedure comprising:

a console comprising a processor and a memory device; and an ultrasonic handpiece comprising a needle coupled with a distal end of the ultrasonic handpiece, wherein the needle comprises a distal end and wherein the ultrasonic handpiece is coupled with the console;

the processor configured to generate a sensing signal through a frequency range centered at a local resonant frequency of the ultrasonic handpiece;

the processor configured to measure impedance characteristics of the sensing signal at the distal end of the needle;

the processor configured to compare the measured impedance characteristics of the generated sensing signal with one or more impedance profiles stored in the memory device;

the processor and the memory device configured to classify, based on the comparison between the measured impedance characteristics and the stored one or more impedance profiles, a medium contacting the distal end of the needle; and the processor configured to control an output of the ultrasonic handpiece based on the classification of the medium contacting the distal end of the needle.

2. The system of claim 1, wherein the measured impedance characteristics comprise impedance magnitude and impedance phase measurements.

3. The system of claim 1, wherein the processor is configured to classify the medium contacting the distal end of the needle using a machine learning algorithm.

4. The system of claim 3, wherein the machine learning algorithm uses, to classify the medium contacting the distal end of the needle, one or more of: a Fuzzy K-Means model, a Support Vector Machine (SVM) model, a Random Forest model, a Nearest Neighbors model, or a Logistic Regression model.

5. The system of claim 1, wherein the processor is configured to compare the measured impedance characteristics of the generated sensing signal with one or more impedance profiles stored in the memory device by calculating deviation values at a plurality of frequencies of the frequency range between the measured impedance characteristics and the one or more stored impedance profiles, wherein the processor is configured to calculate a sum, for each stored impedance profile, of the deviation values at the plurality of frequencies, and to classify the medium contacting the distal end of the needle based on the impedance profile corresponding to the lowest calculated sum.

6. The system of claim 1, wherein the processor is configured to classify the medium contacting the distal end of the needle as one of cataract or non-cataract material.

7. The system of claim 1, wherein, on a condition the medium contacting the distal end of the needle is classified as non-cataract, the processor is configured to control the output of the ultrasonic handpiece by ceasing delivery of ultrasonic power or by preventing delivery of the ultrasonic power.

8. The system of claim 1, wherein the processor is configured to classify the medium contacting the distal end of the needle based on a diameter or gauge of the distal end of the needle.

9. The system of claim 1, wherein the processor is configured to adjust a sensitivity level to be used in classifying the medium contacting the distal end of the needle in response to a user input received at a user interface.

10. The system of claim 1, wherein the processor is configured to determine, based on the classified medium contacting the distal end of the needle, based on aspiration flow data, and based on vacuum pressure data, that an occlusion is present at the distal end of the needle.

11. A method for sensing tissue during a phacoemulsification procedure, the method comprising:

generating a sensing signal through a frequency range centered at a local resonant frequency of an ultrasonic handpiece, wherein the ultrasonic handpiece comprises a needle coupled with the distal end of the ultrasonic handpiece;

measuring impedance characteristics of the sensing signal at a distal end the needle;

comparing the measured impedance characteristics of the generated sensing signal with one or more stored impedance profiles;

classifying, based on the comparison between the measured impedance characteristics and the stored one or more impedance profiles, a medium contacting the distal end of the needle; and controlling an output of the ultrasonic handpiece based on the classification of the medium contacting the distal end of the needle.

12. The method of claim 11, wherein the measured impedance characteristics comprise impedance magnitude and impedance phase measurements.

13. The method of claim 12, further comprising comparing the impedance characteristics of the generated sensing signal with one or more impedance profiles stored in the memory device by calculating deviation values at a plurality of frequencies of the frequency range between the measured impedance characteristics and the one or more stored impedance profiles; and calculating a sum, for each stored impedance profile, of the deviation values at the plurality of frequencies, and classifying the medium contacting the distal end of the needle based on the impedance profile corresponding to the lowest calculated sum.

14. The method of claim 11, further comprising classifying the medium contacting the distal end of the needle using a machine learning algorithm.

15. The method of claim 14, wherein the machine learning algorithm uses, to classify the medium contacting the distal end of the needle, one or more of: a Fuzzy K-Means model, a Support Vector Machine (SVM) model, a Random Forest model, a Nearest Neighbors model, or a Logistic Regression model.

16. The method of claim 11, further comprising classifying the medium contacting the distal end of the needle as one of cataract or non-cataract material.

17. The method of claim 11, wherein, on a condition the medium contacting the distal end of the needle is classified as non-cataract, controlling the output of the ultrasonic handpiece by ceasing delivery of ultrasonic power or by preventing delivery of ultrasonic power.

18. The method of claim 11, further comprising classifying the medium contacting the distal end of the needle based on a diameter or gauge of the distal end of the needle.

19. The method of claim 11, further comprising adjusting a sensitivity level to be used in classifying the medium contacting the distal end of the needle in response to a user input received at a user interface.

20. The method of claim 11, further comprising determining, based on the classified medium contacting the distal end of the needle, based on aspiration flow data, and based on vacuum pressure data, that an occlusion is present at the distal end of the needle.

* * * * *